US010907168B2

(12) United States Patent
D'Aoust et al.

(10) Patent No.: US 10,907,168 B2
(45) Date of Patent: Feb. 2, 2021

(54) JASMONIC ACID PATHWAY ACTIVATOR

(71) Applicants: MEDICAGO INC., Quebec (CA); UNIVERSITE LAVAL, Quebec (CA)

(72) Inventors: Marc-Andre D'Aoust, Quebec (CA); Stephanie Robert, Quebec (CA); Marie-Claire Goulet, Saint-Laurent-Ile-d'Orleans (CA); Dominique Michaud, Quebec (CA); Frank Sainsbury, St. Lucia (AU)

(73) Assignees: MEDICAGO INC., Quebec (CA); UNIVERSITE LAVAL, Quebec (CA)

(*) Notice: Subject to any disclaimer, the term of this patent is extended or adjusted under 35 U.S.C. 154(b) by 0 days.

(21) Appl. No.: 15/740,625

(22) PCT Filed: Jun. 30, 2016

(86) PCT No.: PCT/CA2016/050772
§ 371 (c)(1),
(2) Date: Dec. 28, 2017

(87) PCT Pub. No.: WO2017/000074
PCT Pub. Date: Jan. 5, 2017

(65) Prior Publication Data
US 2018/0195078 A1 Jul. 12, 2018

Related U.S. Application Data

(60) Provisional application No. 62/188,182, filed on Jul. 2, 2015.

(51) Int. Cl.
*C12N 15/82* (2006.01)
(52) U.S. Cl.
CPC ..... *C12N 15/8216* (2013.01); *C12N 15/8257* (2013.01)
(58) Field of Classification Search
None
See application file for complete search history.

(56) References Cited

FOREIGN PATENT DOCUMENTS

| EP | 2708596 A1 | 3/2014 |
| WO | 2012/012462 A2 | 1/2012 |

OTHER PUBLICATIONS

Xue, et al. (Journal of Genetics and Genomics 34.4 (2007): 339-346). (Year: 2007).*
Mason et al. (The Plant Cell, vol. 5, 241-251, Mar. 1993). (Year: 1993).*
Leh et al. (The EMBO Journal vol. 18 No. 24 pp. 7077-7085, 1999). (Year: 1999).*
Sudarshana et al. (Plant Biotechnology Journal (2006) 4, pp. 551-559). (Year: 2006).*
Obembe et al. (Biotechnology Advances 29 (2011) 210-222). (Year: 2011).*
Franceschi, et al. (Proceedings of the National Academy of Sciences 88.15 (1991): 6745-6749). (Year: 1991).*
Kay et al. (Science 236.4806 (1987): 1299-1302). (Year: 1987).*
Omirulleh et al. (Plant molecular biology 21.3 (1993): 415-428). (Year: 1993).*
International Search Report and Written Opinion in International Application No. PCT/CA2016/050772, dated Sep. 20, 2016.
Anand et al., "Salicylic Acid and Systemic Acquired Resistance Play a Role in Attenuating Crown Gall Disease Caused by Agrobacterium tumefaciens," Plant Physiol. 146:703-715 (2008).
Bardor et al., "Immunoreactivity in mammals of two typical plant glyco-epitopes, core $\alpha(1,3)$-fucose and core xylose," Glycobiology 13(6):427-434 (2003).
Benchabane et al., "Companion Protease Inhibitors to Protect Recombinant Proteins in Transgenic Plant Extracts," Meth. Mol. Biol., Recombinant Proteins from Plants 483:265-273 (2009).
Bilgin et al., "Biotic stress globally downregulates photosynthesis genes," Plant Cell Environ. 33:1597-1613 (2010).
Chen et al., "Proteomic identification of differentially expressed proteins in *Arabidopsis* in response to methyl iasmonate," J. Plant Physiol. 168:995-1008 (2011).
D'Aoust et al., "Transient Expression of Antibodies in Plants Using Syringe Agroinfiltration," Meth. Mol. Biol., Recombinant Proteins from Plants 483:41-50 (2009).
Derksen et al., "Signaling cross-talk in plant disease resistance," Plant Sci. 207:79-87 (2013).
Duceppe et al., "Wounding, insect chewing and phloem sap feeding differentially alter the leaf proteome of potato, *Solanum tuberosum* L.," Proteome Sci. 10:73 (2012).
Feys et al., "*Arabidopsis* Mutants Selected for Resistance to the Phytotoxin Coronatine are Male Sterile, Insensitive to Methyl Jasmonate, and Resistant to a Bacterial Pathogen," Plant Cell 6:751-759 (1994).
Figueiredo et al., "Subtilisin-like proteases in plant-pathogen recognition and immune priming: a perspective," Frontiers in Plant Science 5(739):1-4 (2014).
Geada et al., "Detection of Rubisco and mycotoxins as potential contaminants of a plantibody against the hepatitis B surface antigen purified from tobacco," Biologicals 35:309-315 (2007).

(Continued)

*Primary Examiner* — Charles Logsdon
(74) *Attorney, Agent, or Firm* — J.A. Lindeman & Co. PLLC

(57) ABSTRACT

A method of increasing expression of an heterologous protein of interest in a plant or portion of the plant is provided. The method comprises treating the plant or portion of the plant with a jasmonate-pathway activator, and introducing a nucleotide sequence operably linked to a regulatory region derived from a DNA plant virus and encoding the heterologous protein of interest into the plant or portion of the plant. Alternatively, the plant or plant portion may comprise the nucleic acid and encoding the heterologous protein of interest, and the plant or portion of the plant is treated with the jasmonate pathway activator. The treated plant is incubated under conditions to permit expression of the nucleotide sequence encoding the heterologous protein of interest.

13 Claims, 6 Drawing Sheets

Specification includes a Sequence Listing.

(56) References Cited

OTHER PUBLICATIONS

Girard et al., "A multicomponent, elicitor-inducible cystatin complex in tomato, Solanum lycopersicum," New Phytologist 173:841-851 (2007).

Giri et al., "Molecular Interactions between the Specialist Herbivore Manduca sexta (Lepidoptera, Sphingidae) and Its Natural Host Nicotiana attenuata. VII. Changes in the Plant's Proteome," Plant Physiol. 142:1621-1641 (2006).

Goulet et al., "2-DE proteome maps for the leaf apoplast of Nicotiana benthamiana," Proteomics 10:2536-2544 (2010).

Hermsmeier et al., "Molecular Interactions between the Specialist Herbivore Manduca sexta (Lepidoptera, Sphingidae) and Its Natural Host Nicotiana attenuata. I. Large-Scale Changes in the Accumulation of Growth- and Defense-Related Plant mRNAs," Plant Physiol. 125:683-700 (2001).

Hörger et al., "The structural basis of specific protease—inhibitor interactions at the plant—pathogen interface," Curr. Opin. Struct. Biol. 23:842-850 (2013).

Höwing et al., "Endoplasmic reticulum KDEL-tailed cysteine endopeptidase 1 of Arabidopsis (AtCEP1) is involved in pathogen defense," Front. Plant Sci. 5(58):1-11 (2014).

Jung et al., "Agrobacterium tumefaciens mediated transient expression of plant cell wall-degrading enzymes in detached sunflower leaves," Biotechnol. Progr. 30:905-915 (2014).

Jung et al., "Microarray-based screening of jasmonate-responsive genes in Arabidopsis thaliana," Plant Cell Rep. 26:1053-1063 (2007).

Khoudi et al., "Production of a Diagnostic Monoclonal Antibody in Perennial Alfalfa Plants," Biotechnol. Bioeng. 64:135-143 (1999).

Kim et al., "The suppression of the glutelin storage protein gene in transgenic rice seeds results in a higher yield of recombinant protein," Plant Biotechnol. Rep. 6:347-353 (2012).

Lacroix et al., "Will you let me use your nucleus? How Agrobacterium gets its T-DNA expressed in the host plant cell," Can. J. Physiol. Pharmacol. 84:333-345 (2006).

Lawrence et al., "Potato, Solanum tuberosum, Defense Against Colorado Potato Beetle, Leptinotarsa decemlineata (Say): Microarray Gene Expression Profiling of Potato by Colorado Potato Beetle Regurgitant Treatment of Wounded Leaves," J. Chem. Ecol. 34:1013-1025 (2008).

Lorenzo et al., "Jasmonate-INSENSITIVE1 Encodes a MYC Transcription Factor Essential to Discriminate between Different Jasmonate-Regulated Defense Responses in Arabidopsis," Plant Cell 16:1938-1950 (2004).

Mahajan et al., "Stress inducible proteomic changes in Capsicum annuum leaves," Plant Physiol. Biochem. 74:212-217 (2014).

Noir et al., "Jasmonate Controls Leaf Growth by Repressing Cell Proliferation and the Onset of Endoreduplication while Maintaining a Potential Stand-By Mode," Plant Physiol. 161:1930-1951 (2013).

Okada et al., "Jasmonates Induce Both Defense Responses and Communication in Monocotyledonous and Dicotyledonous Plants," Plant Cell Physiol. 56:16-27 (2015).

Peckham et al., "Purification of GFP fusion proteins from transgenic plant cell cultures," Prot. Expres. Purif. 49:183-189 (2006).

Ramirez et al., "An Extracellular Subtilase Switch for Immune Priming in Arabidopsis," PLoS Pathog. 9(6):e1003445 (2013).

Robert et al., "Leaf proteome rebalancing in Nicotiana benthamiana for upstream enrichment of a transiently expressed recombinant protein," Plant Biotech. J. 13:1169-1179 (2015).

Robert-Seilaniantz et al., "Hormone Crosstalk in Plant Disease and Defense: More Than Just Jasmonate-Salicylate Antagonism," Annu. Rev. Phytopathol. 49:317-343 (2011).

Sainsbury et al., "Expression of multiple proteins using full-length and deleted versions of cowpea mosaic virus RNA-2," Plant Biotechnol. J. 6:82-92 (2008).

Schmidt et al., "Proteome rebalancing in soybean seeds can be exploited to enhance foreign protein accumulation," Plant Biotechnol. J. 6:832-842 (2008).

Stanton et al., "Silencing ribulose-1,5-bisphosphate carboxylase/oxygenase expression does not disrupt nitrogen allocation to defense after simulated herbivory in Nicotiana attenuata," Plant Signal. Behav. 8:e27570 (2013).

Thaler et al., "Evolution of jasmonate and salicylate signal crosstalk," Trends Plant Sci. 17:260-270 (2012).

Ullmann-Zeunert et al., "Quantification of growth-defense trade-offs in a common currency: nitrogen required for phenolamide biosynthesis is not derived from ribulose-1,5-bisphosphate carboxylase/oxygenase turnover," Plant J. 75:417-429 (2013).

Veena et al., "Transfer of T-DNA and Vir proteins to plant cells by Agrobacgterium tumefaciens induces expression of host genes involved in mediating transformation and suppresses host defense gene expression," The Plant Journal 35:219-236 (2003).

Vezina et al., "Transient co-expression for fast and high-yield production of antibodies with human-like N-glycans in plants," Plant Biotechnol. J. 7:442-455 (2009).

Wei et al., "Understanding rice plant resistance to the Brown Planthopper (Nilaparvata lugens): A proteomic approach," Proteomics 9:2798-2808 (2009).

Yuan et al., "The plant signal salicylic acid shuts down expression of the vir regulon and activates quormone-quenching genes in Agrobacterium," Proc. Natl. Acad. Sci. 104:11790-11795 (2007).

Zubo et al., "Methyl jasmonate, gibberellic acid, and auxin affect transcription and transcript accumulation of chloroplast genes in barley," J. Plant Physiol. 168:1335-1344 (2011).

Afkar et al., Methyl Jasmonate-Induced Changes in Non- and Antioxidant-Enzymatic Defense in Peppermint (Menthe piperita). Journal of Plant Physiology and Breeding 2013, vol. 3(1), pp. 13-21.

Seema et al., "Effect of Methyl Jasmonate on Sugarcane Seedlings," Sugar Tech. 5(3):189-191 (2003).

Leuzinger et al., "Efficient Agroinfiltration of Plants for High-level Transient Expression of Recombinant Proteins," J. Vis. Exp. 77:e50521 (2013).

Mazarei, M., et al. Pathogen Phytosensing: Plants to Report Plant Pathogens. Sensors, 2008, vol. 8, pp. 2628-2641.

* cited by examiner

Figure 1a
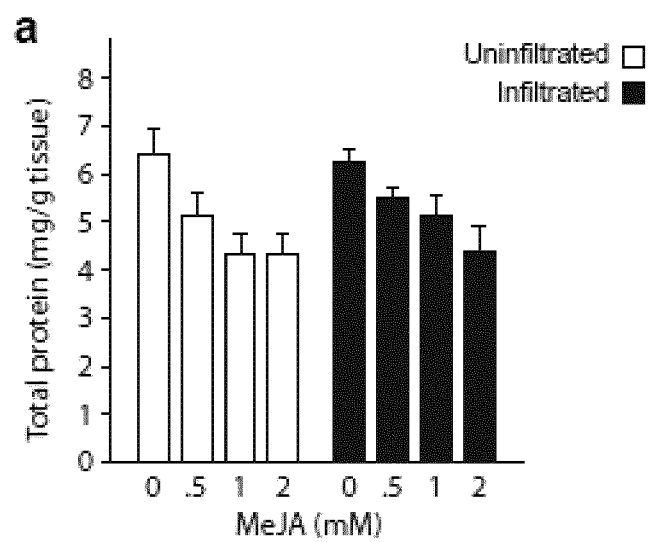
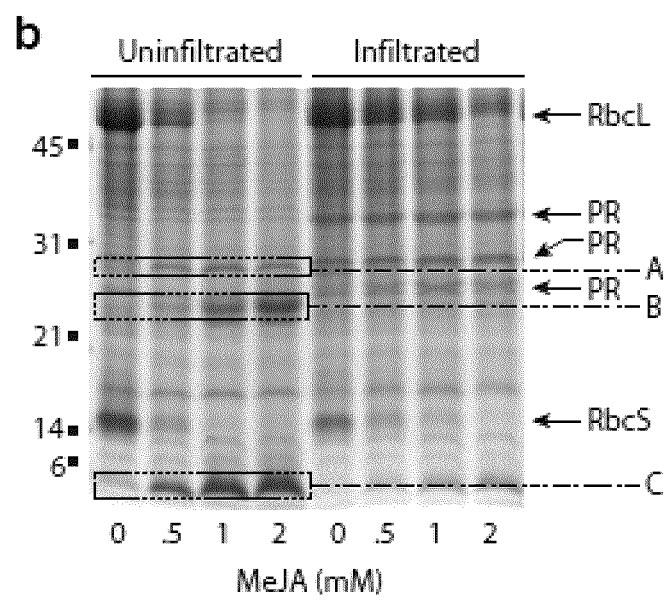
Figure 1b

Figure 1c
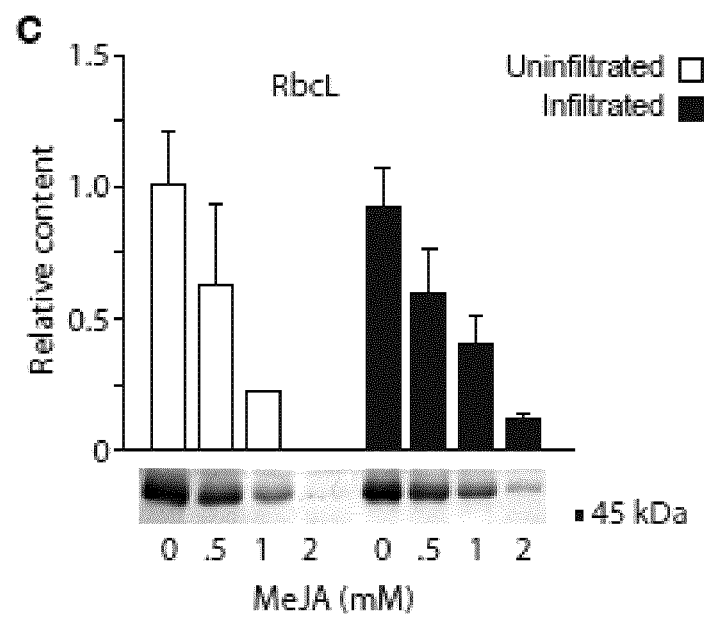
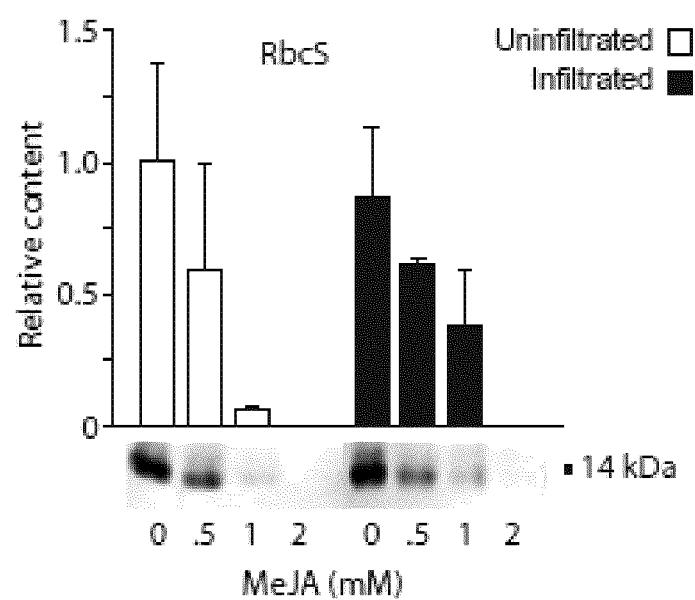
Figure 1d

Figure 2a
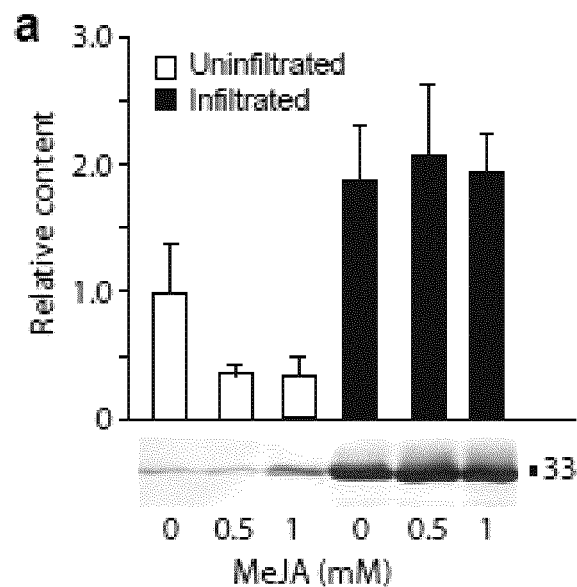
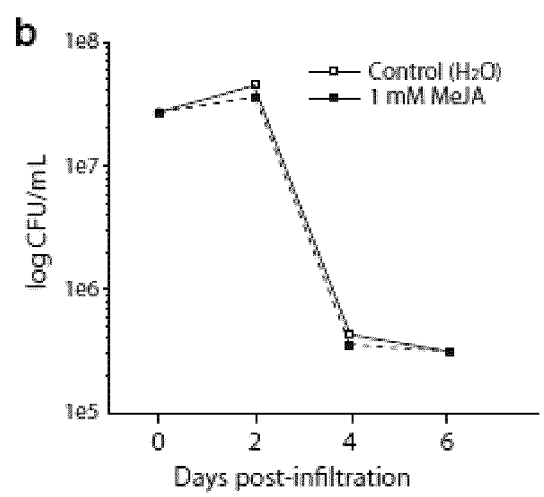
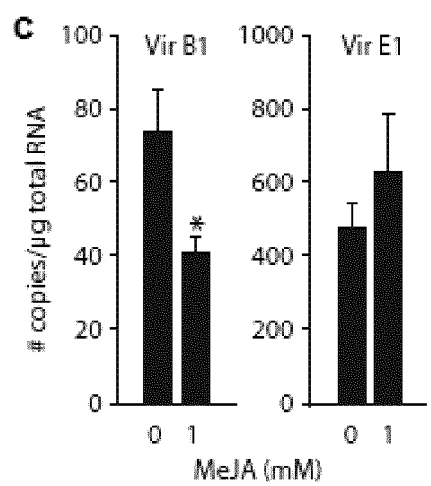
Figure 2b
Figure 2c

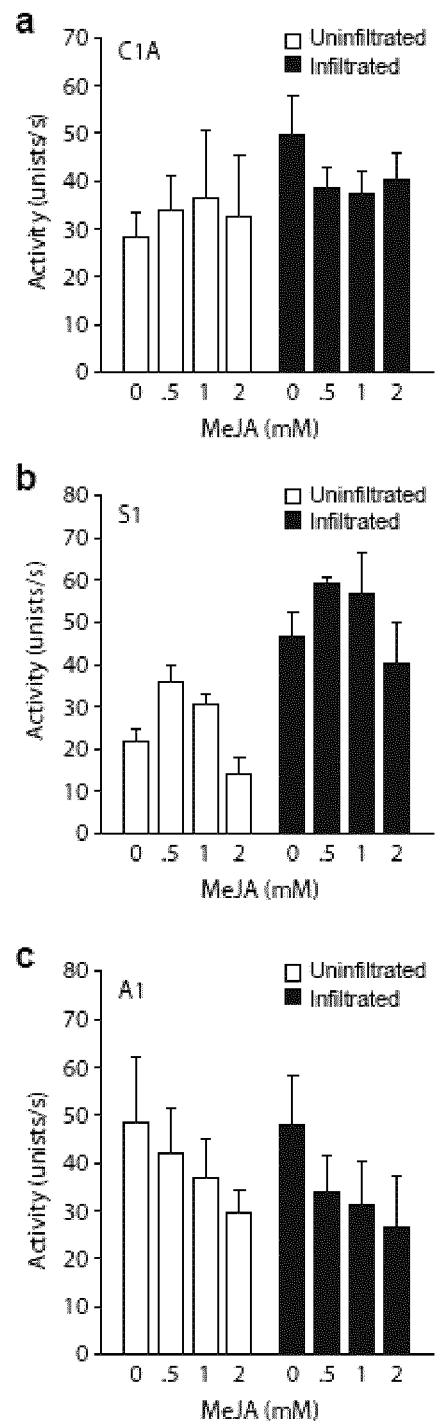
Figures 3a (upper panel), 3b (middle panel), 3c (lower panel)

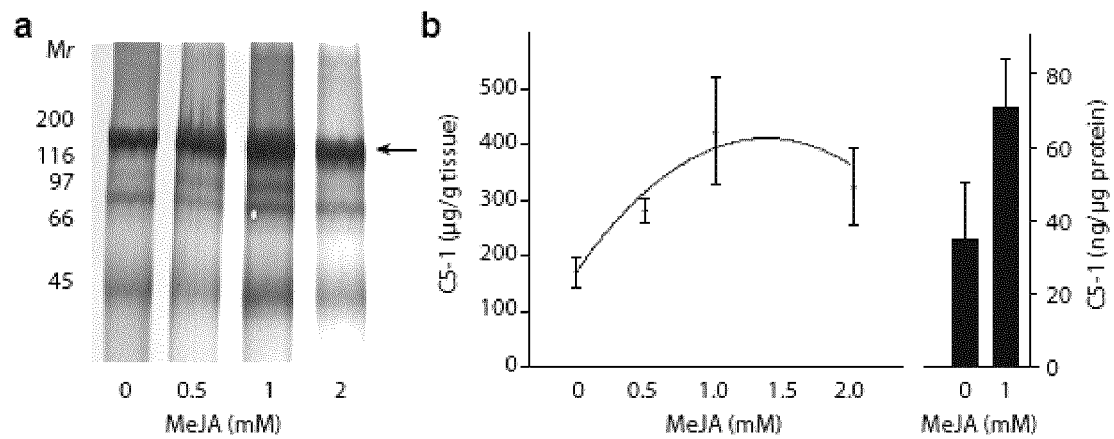
Figure 4a
Figure 4b
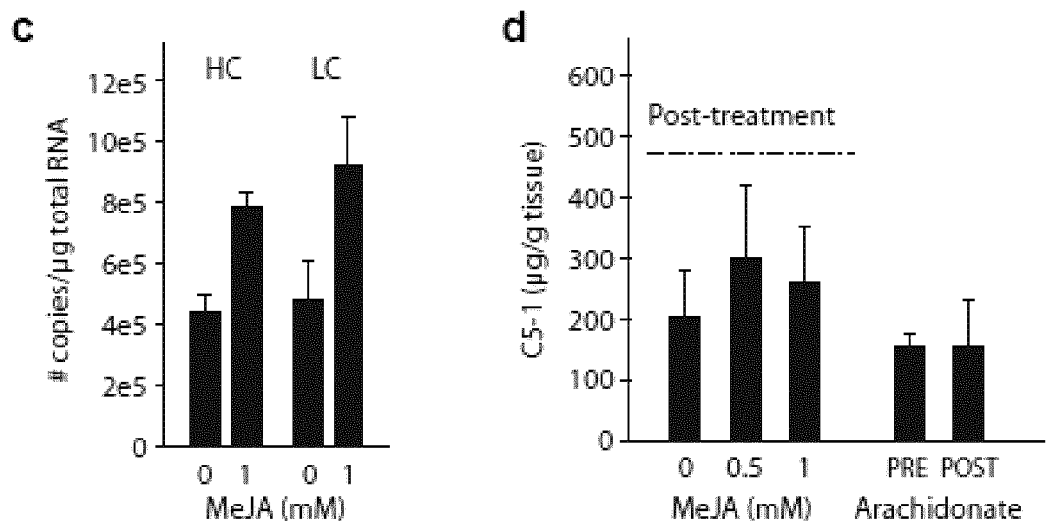
Figure 4c
Figure 4d

SEQUENCE LISTING

```
<160> NUMBER OF SEQ ID NOS: 116

<210> SEQ ID NO 1
<211> LENGTH: 29
<212> TYPE: PRT
<213> ORGANISM: Artificial sequence
<220> FEATURE:
<223> OTHER INFORMATION: consensus amino acid sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid

<400> SEQUENCE: 1

Ile Leu Xaa Ile Tyr Tyr Ser Thr Val Ala Ile Ser Ser Leu Xaa Leu
1               5                   10                  15

Xaa Xaa Met Leu Ala Gly Xaa Ser Xaa Trp Met Cys Ser
            20                  25

<210> SEQ ID NO 2
<211> LENGTH: 69
<212> TYPE: DNA
<213> ORGANISM: Artificial Sequence
<220> FEATURE:
<223> OTHER INFORMATION: nucleotide sequence of PatA SP re GenBank
      Accession A08215

<400> SEQUENCE: 2
atggcaacta ctaaaacttt tttaatttta tttttttatga tattagcaac tactagttca      60
acatgtgct                                                               69
```

```
<210> SEQ ID NO 3
<211> LENGTH: 23
<212> TYPE: PRT
<213> ORGANISM: Artificial Sequence
<220> FEATURE:
<223> OTHER INFORMATION: amino acid sequence of patatin A signal peptide

<400> SEQUENCE: 3

Met Ala Thr Thr Lys Thr Phe Leu Ile Leu Phe Phe Met Ile Leu Ala
1               5                   10                  15

Thr Thr Ser Ser Thr Cys Ala
            20

<210> SEQ ID NO 4
<211> LENGTH: 6
<212> TYPE: DNA
<213> ORGANISM: Artificial Sequence
<220> FEATURE:
<223> OTHER INFORMATION: polyadenylation signal

<400> SEQUENCE: 4 aataaa                                                                      6

<210> SEQ ID NO 5
<211> LENGTH: 20
<212> TYPE: DNA
<213> ORGANISM: Artificial sequence
<220> FEATURE:
<223> OTHER INFORMATION: oligonucleotide primer C5-1 antibody heavy
      chain forward

<400> SEQUENCE: 5
ccaaaacgac accccccatct                                                     20

<210> SEQ ID NO 6
<211> LENGTH: 20
<212> TYPE: DNA
<213> ORGANISM: Artificial Sequence
<220> FEATURE:
<223> OTHER INFORMATION: oligonucleotide primer C5-1 antibody heavy
      chain reverse

<400> SEQUENCE: 6
aggtcactgt cactggctca                                                      20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide primer C5-1 antibody light
      chain forward

<400> SEQUENCE: 7 atccccctcca ggttcagtgg                                                     20

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide primer C5-1 antibody light
      chain reverse

<400> SEQUENCE: 8
cgtgagaggc cagctgttac                                                      20
```

```
<210> SEQ ID NO 9
<211> LENGTH: 20
<212> TYPE: DNA
<213> ORGANISM: Artificial Sequence
<220> FEATURE:
<223> OTHER INFORMATION: Oligonucleotide primer A. tumefaciens VirB1
      forward

<400> SEQUENCE: 9
acgaggcgct aaaatccgaa                                              20

<210> SEQ ID NO 10
<211> LENGTH: 20
<212> TYPE: DNA
<213> ORGANISM: Artificial sequence
<220> FEATURE:
<223> OTHER INFORMATION: Oligonucleotide primer A. tumefaciens VirB1
      reverse

<400> SEQUENCE: 10
gatttgccgt tgtcctggtg                                              20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide primer A.tumefaciens VirE1
      forward

<400> SEQUENCE: 11
gccgatagag agaccggagt                                              20

<210> SEQ ID NO 12
<211> LENGTH: 20
<212> TYPE: DNA
<213> ORGANISM: Artificial sequence
<220> FEATURE:
<223> OTHER INFORMATION: Oligonucleotide primer A.tumefaciens VirE1
      reverse

<400> SEQUENCE: 12
agattgtctt ctgggagcgg                                              20

<210> SEQ ID NO 13
<211> LENGTH: 8
<212> TYPE: PRT
<213> ORGANISM: N. tabacum

<400> SEQUENCE: 13

Gly Pro Ile Gln Leu Thr Asn Arg
1               5

<210> SEQ ID NO 14
<211> LENGTH: 13
<212> TYPE: PRT
<213> ORGANISM: N. tabacum

<400> SEQUENCE: 14

Gly Pro Ile Gln Leu Thr Asn Arg Asn Asn Tyr Glu Lys
1               5                   10

<210> SEQ ID NO 15
<211> LENGTH: 7
<212> TYPE: PRT
```

<213> ORGANISM: N. tabacum

<400> SEQUENCE: 15

Asn Asp Ala Val Glu Asp Arg
1               5

<210> SEQ ID NO 16
<211> LENGTH: 12
<212> TYPE: PRT
<213> ORGANISM: N. tabacum

<400> SEQUENCE: 16

Asn Asp Ala Val Glu Asp Arg Ile Gly Tyr Tyr Arg
1               5                   10

<210> SEQ ID NO 17
<211> LENGTH: 17
<212> TYPE: PRT
<213> ORGANISM: N. tabacum

<400> SEQUENCE: 17

Gln Gly Ile Gly Ser Ile Val Thr Ser Asp Leu Phe Asn Glu Met Leu
1               5                   10                  15

Lys

<210> SEQ ID NO 18
<211> LENGTH: 20
<212> TYPE: PRT
<213> ORGANISM: N. tabacum

<400> SEQUENCE: 18

Arg Tyr Cys Gly Met Leu Asn Val Ala Pro Gly Glu Asn Leu Asp Cys
1               5                   10                  15

Tyr Asn Gln Arg
            20

<210> SEQ ID NO 19
<211> LENGTH: 19
<212> TYPE: PRT
<213> ORGANISM: N. Tabacum

<400> SEQUENCE: 19

Tyr Cys Gly Met Leu Asn Val Ala Pro Gly Glu Asn Leu Asp Cys Tyr
1               5                   10                  15

Asn Gln Arg

<210> SEQ ID NO 20
<211> LENGTH: 12
<212> TYPE: PRT
<213> ORGANISM: N. tabacum

<400> SEQUENCE: 20

Tyr Tyr Gly Arg Gly Pro Ile Gln Leu Thr Asn Arg
1               5                   10

<210> SEQ ID NO 21
<211> LENGTH: 17
<212> TYPE: PRT
<213> ORGANISM: N. tabacum

<400> SEQUENCE: 21

Tyr Tyr Gly Arg Gly Pro Ile Gln Leu Thr Asn Arg Asn Asn Tyr Glu
1               5                   10                  15

Lys

<210> SEQ ID NO 22
<211> LENGTH: 21
<212> TYPE: PRT
<213> ORGANISM: N. benthamiana

<400> SEQUENCE: 22

Ala Leu Met Asp Leu Pro Glu Asn Gly Ser Glu Ser Thr Asp Phe Ile
1               5                   10                  15

Glu Asn Trp Val Lys
            20

<210> SEQ ID NO 23
<211> LENGTH: 14
<212> TYPE: PRT
<213> ORGANISM: N. benthamiana

<400> SEQUENCE: 23

Glu Ile Tyr Asp Lys Asn Pro Glu Leu Ile Asp Glu Leu Lys
1               5                   10

<210> SEQ ID NO 24
<211> LENGTH: 15
<212> TYPE: PRT
<213> ORGANISM: N. benthamiana

<400> SEQUENCE: 24

Glu Ile Tyr Asp Lys Asn Pro Glu Leu Ile Asp Glu Leu Lys Lys
1               5                   10                  15

<210> SEQ ID NO 25
<211> LENGTH: 10
<212> TYPE: PRT
<213> ORGANISM: N. benthamiana

<400> SEQUENCE: 25

Phe Leu Val Phe Ala Cys Ser Asp Ser Arg
1               5                   10

<210> SEQ ID NO 26
<211> LENGTH: 21
<212> TYPE: PRT
<213> ORGANISM: N. benthamiana

<400> SEQUENCE: 26

Ile Asp Glu Ile Thr Ala Glu Leu Gln Thr Ser Gly Phe Gln Ser Val
1               5                   10                  15

His Pro Val Asp Arg
            20

<210> SEQ ID NO 27
<211> LENGTH: 23
<212> TYPE: PRT
<213> ORGANISM: N. benthamiana

<400> SEQUENCE: 27

Ile Asp Glu Ile Thr Ala Glu Leu Gln Thr Ser Gly Phe Gln Ser Val
1               5                   10                  15

His Pro Val Asp Arg Ile Lys
            20

```
<210> SEQ ID NO 28
<211> LENGTH: 10
<212> TYPE: PRT
<213> ORGANISM: N. benthamiana

<400> SEQUENCE: 28

Ile Lys Thr Gly Phe Asp Tyr Phe Lys Lys
1               5                   10

<210> SEQ ID NO 29
<211> LENGTH: 11
<212> TYPE: PRT
<213> ORGANISM: N. benthamiana

<400> SEQUENCE: 29

Asn Ile Ala Asn Met Val Pro Pro Tyr Asp Lys
1               5                   10

<210> SEQ ID NO 30
<211> LENGTH: 13
<212> TYPE: PRT
<213> ORGANISM: N. benthamiana

<400> SEQUENCE: 30

Asn Ile Ala Asn Met Val Pro Pro Tyr Asp Lys Thr Lys
1               5                   10

<210> SEQ ID NO 31
<211> LENGTH: 7
<212> TYPE: PRT
<213> ORGANISM: N. benthamiana

<400> SEQUENCE: 31

Thr Gly Phe Asp Tyr Phe Lys
1               5

<210> SEQ ID NO 32
<211> LENGTH: 8
<212> TYPE: PRT
<213> ORGANISM: N. benthamiana

<400> SEQUENCE: 32

Thr Gly Phe Asp Tyr Phe Lys Lys
1               5

<210> SEQ ID NO 33
<211> LENGTH: 16
<212> TYPE: PRT
<213> ORGANISM: N. benthamiana

<400> SEQUENCE: 33

Val Glu Asn Ile Leu Val Ile Gly His Ser Ala Cys Gly Gly Ile Lys
1               5                   10                  15

<210> SEQ ID NO 34
<211> LENGTH: 18
<212> TYPE: PRT
<213> ORGANISM: N. benthamiana

<400> SEQUENCE: 34

Val Ser Pro Ser His Val Leu Asn Phe Gln Leu Gly Glu Ala Phe Met
1               5                   10                  15

Val Arg
```

<210> SEQ ID NO 35
<211> LENGTH: 9
<212> TYPE: PRT
<213> ORGANISM: N. alata

<400> SEQUENCE: 35

Val Gly Asp Pro Asp Leu Thr Ala Arg
1               5

<210> SEQ ID NO 36
<211> LENGTH: 7
<212> TYPE: PRT
<213> ORGANISM: N. alata

<400> SEQUENCE: 36

Phe Val Thr Thr His Ser Arg
1               5

<210> SEQ ID NO 37
<211> LENGTH: 9
<212> TYPE: PRT
<213> ORGANISM: N. alata

<400> SEQUENCE: 37

Leu Cys Val Asn Gln Thr Val Trp Lys
1               5

<210> SEQ ID NO 38
<211> LENGTH: 12
<212> TYPE: PRT
<213> ORGANISM: N. alata

<400> SEQUENCE: 38

Val Gly Asp Pro Asp Leu Thr Ala Arg Gly Thr Arg
1               5                   10

<210> SEQ ID NO 39
<211> LENGTH: 10
<212> TYPE: PRT
<213> ORGANISM: N. tabacum

<400> SEQUENCE: 39

Ala Ala Gly Ile Thr Ser Ile Gly Val Arg
1               5                   10

<210> SEQ ID NO 40
<211> LENGTH: 10
<212> TYPE: PRT
<213> ORGANISM: N. tabacum

<400> SEQUENCE: 40

Glu Gln Glu Ala Ile Asn Phe Leu Glu Lys
1               5                   10

<210> SEQ ID NO 41
<211> LENGTH: 11
<212> TYPE: PRT
<213> ORGANISM: N. tabacum

<400> SEQUENCE: 41

Gly Lys Asp Ser Val Cys Val Val Thr Gln Lys
1               5                   10

<210> SEQ ID NO 42
<211> LENGTH: 10

<212> TYPE: PRT
<213> ORGANISM: N. tabacum

<400> SEQUENCE: 42

His Ile Thr Ile Phe Ser Pro Glu Gly Arg
1               5                   10

<210> SEQ ID NO 43
<211> LENGTH: 9
<212> TYPE: PRT
<213> ORGANISM: N. Tabacum

<400> SEQUENCE: 43

Leu Phe Gln Val Glu Tyr Ala Phe Lys
1               5

<210> SEQ ID NO 44
<211> LENGTH: 15
<212> TYPE: PRT
<213> ORGANISM: N. tabacum

<400> SEQUENCE: 44

Leu Leu Asp Gln Thr Ser Val Ser His Leu Phe Pro Ile Thr Lys
1               5                   10                  15

<210> SEQ ID NO 45
<211> LENGTH: 7
<212> TYPE: PRT
<213> ORGANISM: N. tabacum

<400> SEQUENCE: 45

Asn Glu Ala Ala Glu Phe Arg
1               5

<210> SEQ ID NO 46
<211> LENGTH: 7
<212> TYPE: PRT
<213> ORGANISM: N. tabacum

<400> SEQUENCE: 46

Thr Leu Val Gln Gln Ala Arg
1               5

<210> SEQ ID NO 47
<211> LENGTH: 18
<212> TYPE: PRT
<213> ORGANISM: N. tabacum

<400> SEQUENCE: 47

Val Leu Thr Thr Glu Glu Ile Asp Glu His Leu Thr Ala Ile Ser Glu
1               5                   10                  15

Arg Asp

<210> SEQ ID NO 48
<211> LENGTH: 14
<212> TYPE: PRT
<213> ORGANISM: N. tabacum

<400> SEQUENCE: 48

Tyr Leu Gly Leu Leu Ala Thr Gly Met Thr Ala Asp Ala Arg
1               5                   10

<210> SEQ ID NO 49
<211> LENGTH: 21

```
<212> TYPE: PRT
<213> ORGANISM: N. plumbaginifolia

<400> SEQUENCE: 49

Ala Ala Ala Ala Thr Gln Phe Gly Ser Gly Trp Ala Trp Leu Ala Tyr
1               5                   10                  15

Lys Pro Glu Glu Lys
            20

<210> SEQ ID NO 50
<211> LENGTH: 22
<212> TYPE: PRT
<213> ORGANISM: N. plumbaginifolia

<400> SEQUENCE: 50

Ala Ala Ala Ala Thr Gln Phe Gly Ser Gly Trp Ala Trp Leu Ala Tyr
1               5                   10                  15

Lys Pro Glu Glu Lys Lys
            20

<210> SEQ ID NO 51
<211> LENGTH: 8
<212> TYPE: PRT
<213> ORGANISM: N. plumbaginifolia

<400> SEQUENCE: 51

Ala Tyr Val Asp Asn Leu Asn Lys
1               5

<210> SEQ ID NO 52
<211> LENGTH: 18
<212> TYPE: PRT
<213> ORGANISM: N. plumbaginifolia

<400> SEQUENCE: 52

Ala Tyr Val Asp Asn Leu Asn Lys Gln Ile Asp Gly Thr Glu Leu Asp
1               5                   10                  15

Gly Lys

<210> SEQ ID NO 53
<211> LENGTH: 10
<212> TYPE: PRT
<213> ORGANISM: N. plumbaginifolia

<400> SEQUENCE: 53

Asp Phe Gly Ser Tyr Asp Ala Phe Val Lys
1               5                   10

<210> SEQ ID NO 54
<211> LENGTH: 13
<212> TYPE: PRT
<213> ORGANISM: N. plumbaginifolia

<400> SEQUENCE: 54

Asp Phe Gly Ser Tyr Asp Ala Phe Val Lys Glu Phe Lys
1               5                   10

<210> SEQ ID NO 55
<211> LENGTH: 21
<212> TYPE: PRT
<213> ORGANISM: N. plumbaginifolia

<400> SEQUENCE: 55
```

```
Lys Phe Glu Leu Gln Pro Pro Pro Tyr Pro Met Asp Ala Leu Glu Pro
1               5                   10                  15

His Met Ser Ser Arg
            20

<210> SEQ ID NO 56
<211> LENGTH: 10
<212> TYPE: PRT
<213> ORGANISM: N. plumbaginifolia

<400> SEQUENCE: 56

Leu Val Ser Trp Glu Ala Val Ser Ser Arg
1               5                   10

<210> SEQ ID NO 57
<211> LENGTH: 10
<212> TYPE: PRT
<213> ORGANISM: N. plumbaginifolia

<400> SEQUENCE: 57

Gln Ile Asp Gly Thr Glu Leu Asp Gly Lys
1               5                   10

<210> SEQ ID NO 58
<211> LENGTH: 22
<212> TYPE: PRT
<213> ORGANISM: N. plumbaginifolia

<400> SEQUENCE: 58

Gln Ile Asp Gly Thr Glu Leu Asp Gly Lys Thr Leu Glu Asp Ile Ile
1               5                   10                  15

Leu Val Thr Tyr Asn Lys
            20

<210> SEQ ID NO 59
<211> LENGTH: 11
<212> TYPE: PRT
<213> ORGANISM: N. plumbaginifolia

<400> SEQUENCE: 59

Arg Pro Asp Tyr Ile Ser Ile Phe Met Glu Lys
1               5                   10

<210> SEQ ID NO 60
<211> LENGTH: 12
<212> TYPE: PRT
<213> ORGANISM: N. plumbaginifolia

<400> SEQUENCE: 60

Thr Leu Glu Asp Ile Ile Leu Val Thr Tyr Asn Lys
1               5                   10

<210> SEQ ID NO 61
<211> LENGTH: 11
<212> TYPE: PRT
<213> ORGANISM: S.lycopersicum

<400> SEQUENCE: 61

Gly Ala Asp Gly Ser Asp Tyr Ile Thr Leu Arg
1               5                   10

<210> SEQ ID NO 62
<211> LENGTH: 15
<212> TYPE: PRT
```

-continued

<213> ORGANISM: S.lycopersicum

<400> SEQUENCE: 62

Lys Pro Leu Ser Val Ser Pro Gly Asn Thr Val Leu Tyr Ser Lys
1               5                   10                  15

<210> SEQ ID NO 63
<211> LENGTH: 12
<212> TYPE: PRT
<213> ORGANISM: S.lycopersicum

<400> SEQUENCE: 63

Thr Ala Gly Gly Leu Leu Leu Thr Glu Ala Ala Lys
1               5                   10

<210> SEQ ID NO 64
<211> LENGTH: 9
<212> TYPE: PRT
<213> ORGANISM: S.lycopersicum

<400> SEQUENCE: 64

Thr Gly Ala Gln Val Ile Tyr Ser Lys
1               5

<210> SEQ ID NO 65
<211> LENGTH: 8
<212> TYPE: PRT
<213> ORGANISM: S.lycopersicum

<400> SEQUENCE: 65

Thr Lys Val Asp Ile Ser Val Lys
1               5

<210> SEQ ID NO 66
<211> LENGTH: 19
<212> TYPE: PRT
<213> ORGANISM: S.lycopersicum

<400> SEQUENCE: 66

Val Ala Glu Ala Glu Glu Lys Thr Ala Gly Gly Leu Leu Leu Thr Glu
1               5                   10                  15

Ala Ala Lys

<210> SEQ ID NO 67
<211> LENGTH: 11
<212> TYPE: PRT
<213> ORGANISM: S.lycopersicum

<400> SEQUENCE: 67

Val Leu Ile Lys Val Ala Glu Ala Glu Glu Lys
1               5                   10

<210> SEQ ID NO 68
<211> LENGTH: 18
<212> TYPE: PRT
<213> ORGANISM: S.lycopersicum

<400> SEQUENCE: 68

Tyr Ala Gly Ser Glu Phe Lys Gly Ala Asp Gly Ser Asp Tyr Ile Thr
1               5                   10                  15

Leu Arg

<210> SEQ ID NO 69

```
<211> LENGTH: 12
<212> TYPE: PRT
<213> ORGANISM: S.lycopersicum

<400> SEQUENCE: 69

Tyr Ala Gly Thr Glu Val Glu Phe Asp Gly Ser Lys
1               5                   10

<210> SEQ ID NO 70
<211> LENGTH: 10
<212> TYPE: PRT
<213> ORGANISM: S.lycopersicum

<400> SEQUENCE: 70

Tyr Thr Thr Leu Lys Pro Leu Gly Asp Arg
1               5                   10

<210> SEQ ID NO 71
<211> LENGTH: 9
<212> TYPE: PRT
<213> ORGANISM: N. alata

<400> SEQUENCE: 71

Val Gly Asp Pro Asp Leu Thr Ala Arg
1               5

<210> SEQ ID NO 72
<211> LENGTH: 7
<212> TYPE: PRT
<213> ORGANISM: N. alata

<400> SEQUENCE: 72

Phe Val Thr Thr His Ser Arg
1               5

<210> SEQ ID NO 73
<211> LENGTH: 9
<212> TYPE: PRT
<213> ORGANISM: N. alata

<400> SEQUENCE: 73

Leu Cys Val Asn Gln Thr Val Trp Lys
1               5

<210> SEQ ID NO 74
<211> LENGTH: 12
<212> TYPE: PRT
<213> ORGANISM: N. alata

<400> SEQUENCE: 74

Val Gly Asp Pro Asp Leu Thr Ala Arg Gly Thr Arg
1               5                   10

<210> SEQ ID NO 75
<211> LENGTH: 23
<212> TYPE: PRT
<213> ORGANISM: N. tabacum

<400> SEQUENCE: 75

Gly Leu Phe Ile Ile Asp Lys Glu Gly Val Ile Gln His Ser Thr Ile
1               5                   10                  15

Asn Asn Leu Gly Ile Gly Arg
            20
```

```
<210> SEQ ID NO 76
<211> LENGTH: 9
<212> TYPE: PRT
<213> ORGANISM: N. tabacum

<400> SEQUENCE: 76

Gly Ser Lys Glu Tyr Phe Ala Ser Ile
1               5

<210> SEQ ID NO 77
<211> LENGTH: 18
<212> TYPE: PRT
<213> ORGANISM: N. tabacum

<400> SEQUENCE: 77

Lys Ser Gly Gly Leu Gly Asp Leu Asn Tyr Pro Leu Ile Ser Asp Val
1               5                   10                  15

Thr Lys

<210> SEQ ID NO 78
<211> LENGTH: 7
<212> TYPE: PRT
<213> ORGANISM: N. tabacum

<400> SEQUENCE: 78

Leu Ser Glu Tyr Ile Gly Lys
1               5

<210> SEQ ID NO 79
<211> LENGTH: 17
<212> TYPE: PRT
<213> ORGANISM: N. tabacum

<400> SEQUENCE: 79

Ser Gly Gly Leu Gly Asp Leu Asn Tyr Pro Leu Ile Ser Asp Val Thr
1               5                   10                  15

Lys

<210> SEQ ID NO 80
<211> LENGTH: 7
<212> TYPE: PRT
<213> ORGANISM: N. tabacum

<400> SEQUENCE: 80

Ser Val Asp Glu Thr Leu Arg
1               5

<210> SEQ ID NO 81
<211> LENGTH: 14
<212> TYPE: PRT
<213> ORGANISM: N. tabacum

<400> SEQUENCE: 81

Ser Tyr Asn Val Leu Ile Pro Asp Gln Gly Ile Ala Leu Arg
1               5                   10

<210> SEQ ID NO 82
<211> LENGTH: 25
<212> TYPE: PRT
<213> ORGANISM: N. tabacum

<400> SEQUENCE: 82

Thr Leu Gln Ala Leu Gln Tyr Val Gln Asp Asn Pro Asp Glu Val Cys
1               5                   10                  15
```

```
Pro Ala Gly Trp Lys Pro Gly Glu Lys
            20                  25

<210> SEQ ID NO 83
<211> LENGTH: 25
<212> TYPE: PRT
<213> ORGANISM: N. tabacum

<400> SEQUENCE: 83

Cys Pro Asp Ala Tyr Ser Tyr Pro Gln Asp Asp Pro Thr Ser Leu Phe
1               5                   10                  15

Thr Cys Pro Ser Gly Thr Asn Tyr Arg
            20                  25

<210> SEQ ID NO 84
<211> LENGTH: 10
<212> TYPE: PRT
<213> ORGANISM: N. tabacum

<400> SEQUENCE: 84

Thr Asn Cys Asn Phe Asp Gly Ser Gly Arg
1               5                   10

<210> SEQ ID NO 85
<211> LENGTH: 20
<212> TYPE: PRT
<213> ORGANISM: N. tabacum

<400> SEQUENCE: 85

Thr Asn Glu Tyr Cys Cys Thr Asn Gly Pro Gly Ser Cys Gly Pro Thr
1               5                   10                  15

Asp Leu Ser Arg
            20

<210> SEQ ID NO 86
<211> LENGTH: 13
<212> TYPE: PRT
<213> ORGANISM: N. tabacum

<400> SEQUENCE: 86

Thr Gln Gly Gly Cys Asn Asn Pro Cys Thr Val Ile Lys
1               5                   10

<210> SEQ ID NO 87
<211> LENGTH: 9
<212> TYPE: PRT
<213> ORGANISM: N. tabacum

<400> SEQUENCE: 87

Asp Gly Ala Ser Gly Gly Val Val Arg
1               5

<210> SEQ ID NO 88
<211> LENGTH: 15
<212> TYPE: PRT
<213> ORGANISM: N. tabacum

<400> SEQUENCE: 88

Ser Gly Ser Ala Ala Asp Ser Gln Ile Val Ser Asp Tyr Val Arg
1               5                   10                  15

<210> SEQ ID NO 89
<211> LENGTH: 10
```

```
<212> TYPE: PRT
<213> ORGANISM: N. tabacum

<400> SEQUENCE: 89

Thr Ser Thr Gly Met Tyr Val Ala Asn Arg
1               5                   10

<210> SEQ ID NO 90
<211> LENGTH: 17
<212> TYPE: PRT
<213> ORGANISM: N. tabacum

<400> SEQUENCE: 90

Tyr Phe Leu His Gln His Thr Ile Gln Leu Gly Gln Pro Ala Thr Val
1               5                   10                  15
Lys

<210> SEQ ID NO 91
<211> LENGTH: 21
<212> TYPE: PRT
<213> ORGANISM: N. plumbaginifolia

<400> SEQUENCE: 91

Ala Ala Ala Ala Thr Gln Phe Gly Ser Gly Trp Ala Trp Leu Ala Tyr
1               5                   10                  15
Lys Pro Glu Glu Lys
            20

<210> SEQ ID NO 92
<211> LENGTH: 8
<212> TYPE: PRT
<213> ORGANISM: N. plumbaginifolia

<400> SEQUENCE: 92

Ala Tyr Val Asp Asn Leu Asn Lys
1               5

<210> SEQ ID NO 93
<211> LENGTH: 18
<212> TYPE: PRT
<213> ORGANISM: N. plumbaginifolia

<400> SEQUENCE: 93

Ala Tyr Val Asp Asn Leu Asn Lys Gln Ile Asp Gly Thr Glu Leu Asp
1               5                   10                  15
Gly Lys

<210> SEQ ID NO 94
<211> LENGTH: 10
<212> TYPE: PRT
<213> ORGANISM: N. plumbaginifolia

<400> SEQUENCE: 94

Asp Phe Gly Ser Tyr Asp Ala Phe Val Lys
1               5                   10

<210> SEQ ID NO 95
<211> LENGTH: 13
<212> TYPE: PRT
<213> ORGANISM: N. plumbaginifolia

<400> SEQUENCE: 95

Asp Phe Gly Ser Tyr Asp Ala Phe Val Lys Glu Phe Lys
```

```
<210> SEQ ID NO 96
<211> LENGTH: 21
<212> TYPE: PRT
<213> ORGANISM: N. plumbaginifolia

<400> SEQUENCE: 96

Lys Phe Glu Leu Gln Pro Pro Tyr Pro Met Asp Ala Leu Glu Pro
1               5                   10                  15

His Met Ser Ser Arg
            20

<210> SEQ ID NO 97
<211> LENGTH: 10
<212> TYPE: PRT
<213> ORGANISM: N. plumbaginifolia

<400> SEQUENCE: 97

Leu Val Ser Trp Glu Ala Val Ser Ser Arg
1               5                   10

<210> SEQ ID NO 98
<211> LENGTH: 10
<212> TYPE: PRT
<213> ORGANISM: N. plumbaginifolia

<400> SEQUENCE: 98

Gln Ile Asp Gly Thr Glu Leu Asp Gly Lys
1               5                   10

<210> SEQ ID NO 99
<211> LENGTH: 22
<212> TYPE: PRT
<213> ORGANISM: N. plumbaginifolia

<400> SEQUENCE: 99

Gln Ile Asp Gly Thr Glu Leu Asp Gly Lys Thr Leu Glu Asp Ile Ile
1               5                   10                  15

Leu Val Thr Tyr Asn Lys
            20

<210> SEQ ID NO 100
<211> LENGTH: 11
<212> TYPE: PRT
<213> ORGANISM: N. plumbaginifolia

<400> SEQUENCE: 100

Arg Pro Asp Tyr Ile Ser Ile Phe Met Glu Lys
1               5                   10

<210> SEQ ID NO 101
<211> LENGTH: 12
<212> TYPE: PRT
<213> ORGANISM: N. plumbaginifolia

<400> SEQUENCE: 101

Thr Leu Glu Asp Ile Ile Leu Val Thr Tyr Asn Lys
1               5                   10

<210> SEQ ID NO 102
<211> LENGTH: 14
<212> TYPE: PRT
<213> ORGANISM: N. tabacum
```

```
<400> SEQUENCE: 102

Ala Cys Ile Ser Glu Lys Phe Thr Asp Gly His Cys Ser Lys
1               5                   10

<210> SEQ ID NO 103
<211> LENGTH: 8
<212> TYPE: PRT
<213> ORGANISM: N. tabacum

<400> SEQUENCE: 103

Phe Thr Asp Gly His Cys Ser Lys
1               5

<210> SEQ ID NO 104
<211> LENGTH: 7
<212> TYPE: PRT
<213> ORGANISM: N. tabacum

<400> SEQUENCE: 104

Lys Ala Cys Ile Ser Glu Lys
1               5

<210> SEQ ID NO 105
<211> LENGTH: 15
<212> TYPE: PRT
<213> ORGANISM: N. tabacum

<400> SEQUENCE: 105

Lys Ala Cys Ile Ser Glu Lys Phe Thr Asp Gly His Cys Ser Lys
1               5                   10                  15

<210> SEQ ID NO 106
<211> LENGTH: 14
<212> TYPE: PRT
<213> ORGANISM: N. tabacum

<400> SEQUENCE: 106

Ala Cys Ile Ser Glu Lys Phe Thr Asp Gly His Cys Ser Lys
1               5                   10

<210> SEQ ID NO 107
<211> LENGTH: 6
<212> TYPE: PRT
<213> ORGANISM: N. tabacum

<400> SEQUENCE: 107

Ala Cys Ile Ser Glu Lys
1               5

<210> SEQ ID NO 108
<211> LENGTH: 9
<212> TYPE: PRT
<213> ORGANISM: N. benthamiana

<400> SEQUENCE: 108

Gly Cys Thr Phe Glu Cys Asp Pro Arg
1               5

<210> SEQ ID NO 109
<211> LENGTH: 9
<212> TYPE: PRT
<213> ORGANISM: N. benthamiana

<400> SEQUENCE: 109
```

```
Ile Cys Thr Asn Cys Cys Ala Gly Lys
1               5

<210> SEQ ID NO 110
<211> LENGTH: 10
<212> TYPE: PRT
<213> ORGANISM: N. benthamiana

<400> SEQUENCE: 110

Leu Cys Thr Asn Cys Cys Ala Gly Thr Lys
1               5                   10

<210> SEQ ID NO 111
<211> LENGTH: 12
<212> TYPE: PRT
<213> ORGANISM: N. benthamiana

<400> SEQUENCE: 111

Asn Arg Leu Cys Thr Asn Cys Cys Ala Gly Thr Lys
1               5                   10

<210> SEQ ID NO 112
<211> LENGTH: 17
<212> TYPE: PRT
<213> ORGANISM: N. benthamiana

<400> SEQUENCE: 112

Tyr Phe Ser Asp Asp Gly Thr Phe Val Cys Glu Gly Glu Ser Asp Pro
1               5                   10                  15

Arg

<210> SEQ ID NO 113
<211> LENGTH: 20
<212> TYPE: PRT
<213> ORGANISM: N. benthamiana

<400> SEQUENCE: 113

Tyr Phe Ser Asp Asp Gly Thr Phe Val Cys Glu Gly Glu Ser Asp Pro
1               5                   10                  15

Arg Asn Pro Lys
            20

<210> SEQ ID NO 114
<211> LENGTH: 24
<212> TYPE: PRT
<213> ORGANISM: N. benthamiana

<400> SEQUENCE: 114

Tyr Phe Ser Asp Asp Gly Thr Phe Val Cys Glu Gly Glu Ser Asp Pro
1               5                   10                  15

Arg Asn Pro Lys Pro Cys Pro Arg
            20

<210> SEQ ID NO 115
<211> LENGTH: 9
<212> TYPE: PRT
<213> ORGANISM: N. benthamiana

<400> SEQUENCE: 115

Ile Ala Tyr Gly Ile Cys Pro Leu Ser
1               5
```

```
<210> SEQ ID NO 116
<211> LENGTH: 8
<212> TYPE: PRT
<213> ORGANISM: N. benthamiana

<400> SEQUENCE: 116

Ile Ala Tyr Gly Val Cys Pro Arg
1               5
```

JASMONIC ACID PATHWAY ACTIVATOR

FIELD OF INVENTION

The present invention relates to protein production in plants. This invention also relates to use of a jasmonic acid pathway activator to increase heterologous protein production in a plant or portion of a plant.

BACKGROUND OF THE INVENTION

Plants are increasingly being used as bio-factories for the production of clinically useful recombinant proteins. Advantages associated with plant-produced recombinant protein expression, include mammalian-like post-translational maturation of protein backbones, low infrastructure costs (compared to classical systems based on industrial-scale fermenters), and reduced biosafety issues regarding product contamination with microbial toxins or human pathogens Approaches to enrich recombinant proteins in plant extracts often rely on the choice of a proper extraction buffer pH or ionic strength, to preferentially remove host proteins and facilitate further purification. Ammonium sulfate precipitation and extraction at low pH are useful in green tissue extracts to precipitate contaminants like cellular debris and photosynthetic pigments. These procedures are also useful to precipitate the highly abundant enzyme ribulose 1,5-bisphosphate carboxylase oxygenase (RuBisCO) (Peckham et al., 2006), which represents up to 50% of total soluble proteins (TSP) in leaves and often complicates the preparation of a highly purified protein product (e.g. Gaeda et al., 2007).

Methyl jasmonate (MeJA) is a volatile derivative of the stress hormone jasmonic acid (Okada et al., 2015). Down-regulating effects for MeJA and jasmonic acid-inducing signals such as wounding, herbivory or insect oral secretions on the transcription of photosynthesis-related genes have been reported (Hermsmeier et al., 2001; Jung et al., 2007; Bilgin et al., 2010; Zubo et al., 2011; Duceppe et al., 2012). MeJA was also shown to promote an elevated expression of ribosomal genes in leaves, presumably useful in keeping the protein biosynthesis machinery active in cells responding to the jasmonate signaling pathway (Noir et al., 2013).

SUMMARY OF THE INVENTION

The present invention relates to protein production in plants. This invention also relates to use of a jasmonic acid pathway activator to increase protein production in a plant or portion of a plant.

It is an object of the invention to provide an improved method of producing heterologous protein of interest within a plant or a portion of the plant.

A method (A) of increasing expression of an heterologous protein of interest in a plant or portion of the plant is described. The method comprises:
  i) treating the plant or portion of the plant with a jasmonate-pathway activator;
  ii) introducing a nucleotide sequence comprising a nucleic acid encoding the heterologous protein of interest and operably linked to a regulatory region derived from a DNA plant virus; into the plant or portion of the plant; and
  iii) incubating the plant or the portion of the plant under conditions to permit expression of the nucleotide sequence encoding the heterologous protein of interest, the increase in expression observed when an amount of the heterologous protein of interest extracted from the plant or portion of the plant is compared to the heterologous protein of interest produced in a second plant or portion of the second plant that comprises the same nucleotide sequence and has been not been treated with the jasmonate-pathway activator.

The DNA plant virus described in the method (A) outlined above may be an insect-born DNA plant virus. Furthermore, the jasmonate-pathway activator described in the method (A) above may be methyl jasmonate, jasmonic acid, coronatine, or any biologically active derivative of methyl jasmonate, jasmonic acid or coronatine.

Also described herein is a method (A) as defined above, wherein in the step of treating (step i), the jasmonic pathway activator is applied as a gas to the plant or portion of the plant, or a liquid and sprayed onto the plant or portion of the plant, or added to growth media supporting the plant or portion of the plant. Alternatively, the step of treating (step i) and introducing (step ii) may be combined so that the jasmonic pathway activator is introduced into the plant or portion of the plant along with the nucleotide sequence.

The jasmonic-pathway activator use in the method (A) described above, may be a gas, or a liquid.

Further, there is provided a method (A) as defined above, wherein the nucleotide sequence is introduced into the plant or portion of the plant in a transient manner using a liquid medium within which the plant or portion of the plant is immersed, and the jasmonic-pathway activator is introduced into the liquid medium in the step of treating (step i). Alternatively, the steps of treating (step i) and introducing (step ii) may be combined so that the jasmonic pathway activator is introduced into the liquid medium along with the nucleotide sequence, and the jasmonic-pathway activator and nucleotide sequence are introduced into the plant or portion of the plant together.

Also provided is a method (B) of decreasing total host soluble protein in a plant or portion of the plant comprising,
  i) treating the plant or portion of the plant with a jasmonate-pathway activator;
  ii) introducing a nucleotide sequence comprising a nucleic acid encoding a heterologous protein of interest and operably linked to a regulatory region derived from a DNA plant virus into the plant or portion of the plant; and
  iii) incubating the plant or the portion of a plant under conditions to permit expression of the nucleotide sequence encoding the heterologous protein of interest, the decrease of total host protein observed when an amount of the total host protein extracted from the plant or portion of the plant is compared to the total host protein produced in a second plant or portion of the second plant that comprises the same nucleotide sequence but that has been not been treated with the jasmonate-pathway activator.

The DNA plant virus described in the method (B) outlined above may be an insect-born DNA plant virus. Furthermore, the jasmonate-pathway activator described in the method above may be methyl jasmonate, jasmonic acid, coronatine, or any biologically active derivative of methyl jasmonate, jasmonic acid or coronatine.

Also described herein is a method (B) as defined above, wherein in the step of treating (step i), the jasmonic pathway activator is applied as a gas to the plant or portion of the plant, or a liquid and sprayed onto the plant or portion of the plant, or added to growth media supporting the plant or portion of the plant. Alternatively, the step of treating (step i) and introducing (step ii) may be combined so that the jasmonic pathway activator is introduced into the plant or portion of the plant along with the nucleotide sequence.

The jasmonic-pathway activator use in the method (B) described above, may be a gas, or a liquid.

Further, there is provided a method (B) as defined above, wherein the nucleotide sequence is introduced into the plant or portion of the plant in a transient manner using a liquid medium within which the plant or portion of the plant is immersed, and the jasmonic-pathway activator is introduced into the liquid medium in the step of treating (step i). Alternatively, the steps of treating (step i) and introducing (step ii) may be combined so that the jasmonic pathway activator is introduced into the liquid medium along with the nucleotide sequence, and the jasmonic-pathway activator and nucleotide sequence are introduced into the plant or portion of the plant together.

Additionally, a method (C) is provided to increase expression of an heterologous protein of interest in a transgenic plant or portion of the transgenic plant comprising, i) treating the transgenic plant or portion of the transgenic plant with a jasmonate-pathway activator, the transgenic plant or portion of the transgenic plant comprising a nucleotide sequence encoding the heterologous protein of interest operably linked to a regulatory region derived from a DNA plant virus; and ii) incubating the transgenic plant or the portion of the transgenic plant under conditions to permit expression of the nucleotide sequence encoding the heterologous protein of interest, the increase in expression observed when an amount of the heterologous protein of interest extracted from the transgenic plant or portion of the transgenic plant is compared to the heterologous protein of interest produced in a second transgenic plant or portion of the second transgenic plant that comprises the same nucleotide sequence and has been not been treated with the jasmonate-pathway activator.

The jasmonate-pathway activator described in the method (C) above may be methyl jasmonate, jasmonic acid, coronatine, or any biologically active derivative of methyl jasmonate, jasmonic acid or coronatine.

Also described herein is a method (C) as defined above, wherein in the step of treating (step i), the jasmonic pathway activator is applied as a gas to the transgenic plant or portion of the transgenic plant, or a liquid and sprayed onto the transgenic plant or portion of the transgenic plant, or added to growth media supporting the transgenic plant or portion of the transgenic plant.

The use of the jasmonic pathway activator, for example, methyl jasmonate (MeJA), to elicite an enrichment of a recombinant, heterologous protein of interest is described herein. Overall efficiency of downstream processing of heterologous proteins expressed in a plant, including purification yield and contamination of the final product with host proteins or their proteolytic fragments, reducing protein degradation in crude extracts or culture media, and optimizing recovery schemes for protein enrichment may be improved by adjusting the ratio of recombinant to host (native) proteins. As described herein, application of a jasmonic pathway activator was found to alter the proteome in leaves of plants. Without wishing to be bound by theory, this alteration may impact the specific and relative yields of the production of a heterologous protein of interest in plant tissue. MeJA treatment induced a depletion of RuBisCO large and small subunit pools, and increased levels of jasmonate-inducible defense proteins (for example, thionins, Ser protease inhibitors and antimicrobial hydrolases). The increase in jasmonate-inducible defense proteins was reduced with agroinfiltration. However, a RuBisCO-depleted cellular environment was maintained in agroinfiltrated leaves, allowing for an effective enrichment of heterologous proteins of interest.

Compared to plants that were not treated with a jasmonic pathway activator, treatment using a jasmonic pathway activator results in an increased expression of a heterologous protein of interest. Additionally, treatment using a jasmonic pathway activator results in an approximately fivefold enrichment for a transiently expressed heterologous protein of interest relative to RuBisCO. The five fold enrichment of the heterologous protein of interest results from a greater than twofold depletion of RuBisCO and an approx. twofold increase in the heterologous protein of interest mRNA transcripts, and an approx. twofold increase in heterologous protein of interest levels on a fresh weight basis.

Therefore, treating a plant or portion of a plant with a jasmonic pathway activator results in an overall increase in yield of a heterologous protein of interest, and a relative increase in yield of a heterologous protein of interest compared to the levels of RuBisCO. By reducing RuBisCO levels, extraction and purification of the heterologous protein of interest may also be simplified due to reduced background protein contamination during the extraction process.

This summary of the invention does not necessarily describe all features of the invention.

BRIEF DESCRIPTION OF THE DRAWINGS

These and other features of the invention will become more apparent from the following description in which reference is made to the appended drawings wherein:

FIGS. 1a-1d show total soluble proteins (TSP), 1-D proteome profile and RuBisCO subunit levels in agroinfiltrated and control N. benthamiana leaves treated with the stress elicitor MeJA 24 h before infection. FIG. 1a shows TSP on a fresh weight basis in leaves treated with 0, 0.5, 1 or 2 mM MeJA. FIG. 1b shows Coomassie blue-stained protein profile in control and MeJA-treated leaves following SDS-PAGE. Mr, commercial molecular mass markers; PR, pathogenesis-related proteins up-regulated in agroinfiltrated leaves; RbcL and RbcS, RuBisCO large and small subunit, respectively; A, B and C boxes, gel areas containing MeJA-inducible proteins in uninfiltrated plants (see Table 2 for protein identities). FIGS. 1c and 1d show relative amounts of RuBisCO large (RbcL; FIG. 1c) and small (RbsS; FIG. 1d) subunits in MeJA-treated leaves as determined by densitometry following immunodetection with appropriate antibodies. Protein signals on the immunoblots were quantified using the Phoretix 2-D Expression software v. 2005 (Non-Linear USA, Durham N.C., U.S.A.) after scanning nitrocellulose membranes with a Microtek ScanMaker II digitalizer (Microtek Laboratory, Torrance Calif., U.S.A.). Data are expressed as relative levels compared to non-treated controls assigned an arbitrary level of 1.0. Each bar on panels (a) and (c) is the mean of three independent (leaf replicate) values±SE. Infiltrated leaves were transfected with A. tumefaciens cells 24 h post-MeJA treatment. All plant samples were harvested seven days post-MeJA treatment (i.e. six days post-agroinfiltration for the transfected plants).

FIGS. 2a-2c show the effect of MeJA treatment on PR-2 protein accumulation, agrobacteria numbers and transcript numbers of the two A. tumefaciens virulence proteins VirB1 and VirE1 in N. benthamiana leaves. FIG. 2a shows the effects of MeJA treatment on accumulation of the 33-kDa, pathogen-inducible PR-2 protein in control and agroinfiltrated leaves as assayed by densitometry following immunodetection. Immunoblot signals were quantified using the Phoretix 2-D Expression software v. 2005 (NonLinear USA) after scanning nitrocellulose membranes with a Microtek ScanMaker II digitalizer (Microtek Laboratory). Data are the mean of three leaf replicates±SE. An arbitrary value of 1.0 was assigned to PR-2 level in control healthy leaves. FIG. 2b shows bacteria retrieved from *N. benthamiana* leaves 0, 2, 4 or 6 days post-agroinfiltration. Data are expressed as log numbers of colony-forming units (CFU) on agar plates and each point is the mean of five independent (leaf replicate) values±SE. FIG. 2c shows mRNA transcript numbers for VirB1 and VirE1 in agroinfiltrated leaves treated with 0 or 1 mM MeJA, as assayed by real-time RT PCR with appropriate DNA primers. Each value is the mean of five biological (leaf replicate) values±SE. Asterisk indicates a significantly lower value for VirB1 transcripts in MeJA-treated leaves compared to control leaves (Student's t-test; P<0.05).

FIGS. 3a-3c show protease activities in crude protein extracts of control and agroinfiltrated *N. benthamiana* leaves treated with 0, 0.5, 1 or 2 mM MeJA 24 h before infiltration. Protease assays were conducted in vitro using fluorigenic peptide substrates specific to cathepsin L-like (C1A) Cys proteases (FIG. 3a), trypsin-like (S1) Ser proteases (FIG. 3b), and cathepsin D/E-like (A1) Asp proteases (FIG. 3c), Leaf samples were harvested seven days post-MeJA treatment. Each bar is the mean of three independent (leaf replicate) values±SE.

FIGS. 4a-4d show C5-1 antibody yield and expression in agroinfiltrated *N. benthamiana* leaves treated with 0, 0.5, 1 or 2 mM MeJA. FIG. 4a shows C5-1 heavy and light chain full (arrow) and partial complexes immunodetected following SDS-PAGE in non-reducing conditions. Mr, commercial molecular mass markers. FIG. 4b shows ELISA-assayed C5-1 in MeJA-treated leaves. Data are expressed on a weight basis (quadratic curve; $r^2$=0.885) or on a relative basis compared to total soluble proteins (histogram). FIG. 4c shows mRNA transcripts for C5-1 light (LC) and heavy (HC) chains in leaves treated with 0 or 1 mM MeJA, as assayed by real-time RT PCR. FIG. 4d shows ELISA-assayed C5-1 in leaves treated with 0, 0.5 or 1 mM MeJA 24 h after infiltration or with 1 mM arachidonic acid 24 h before or after infiltration. Each bar or point on panels (b), (c) and (d) is the mean of five independent (leaf replicate) values±SE.

DETAILED DESCRIPTION

Figure 5:
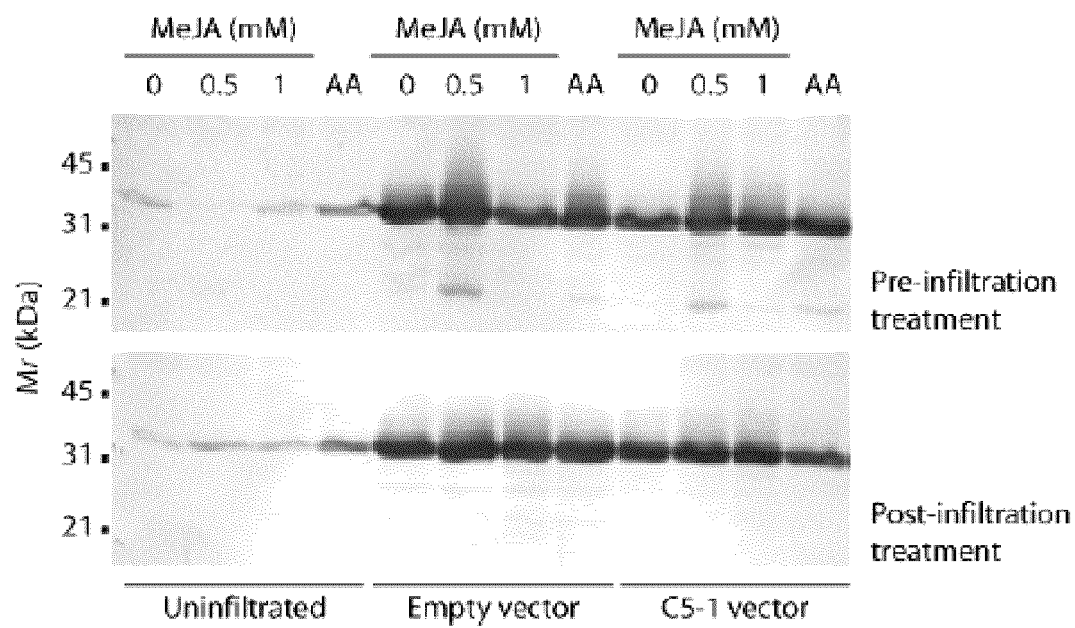
FIG. 5 shows imunodetection of *N. benthamiana* 33-kDa PR-2 protein in crude protein extracts of control and agroinfected leaves treated with 0, 0.5 or 1 mm MeJA, or with 1 mM arachidonic acid (AA), 24 h before (upper panel) or after (lower panel) agroinfiltration. Mr, molecular mass markers. Agroinfiltrations included treatments with *A. tumefaciens* harbouring either a pcambia2300 'empty vector' or the C5-1—encoding vector.
Figure 6:
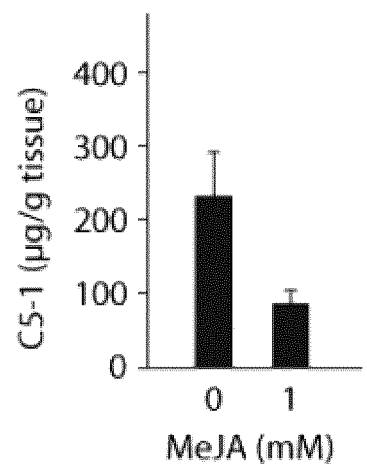
FIG. 6 shows C5-1 antibody yield in agroinfiltrated *N. benthamiana* leaves treated with 0 or 1 mM MeJA. The coding sequences of C5-1 antibody light and heavy chains were expressed under the control of the alfalfa plastocyanin promoter (U.S. Pat. No. 7,125,978, which is incorporated herein by reference). Data are presented on a leaf weight basis. Each bar is the mean of five independent (leaf replicate) values±se.

The following description is of a preferred embodiment.

The present invention relates to protein production in plants. This invention also relates to use of a jasmonic acid pathway activator to increase protein production in a plant or portion of a plant.

As used herein, the terms "comprising," "having," "including" and "containing," and grammatical variations thereof, are inclusive or open-ended and do not exclude additional, un-recited elements and/or method steps. The term "consisting essentially of" when used herein in connection with a use or method, denotes that additional elements and/or method steps may be present, but that these additions do not materially affect the manner in which the recited method or use functions. The term "consisting of" when used herein in connection with a use or method, excludes the presence of additional elements and/or method steps. A use or method described herein as comprising certain elements and/or steps may also, in certain embodiments consist essentially of those elements and/or steps, and in other embodiments consist of those elements and/or steps, whether or not these embodiments are specifically referred to. In addition, the use of the singular includes the plural, and "or" means "and/or" unless otherwise stated. The term "plurality" as used herein means more than one, for example, two or more, three or more, four or more, and the like. Unless otherwise defined herein, all technical and scientific terms used herein have the same meaning as commonly understood by one of ordinary skill in the art. As used herein, the term "about" refers to an approximately +/−10% variation from a given value. It is to be understood that such a variation is always included in any given value provided herein, whether or not it is specifically referred to. The use of the word "a" or "an" when used herein in conjunction with the term "comprising" may mean "one," but it is also consistent with the meaning of "one or more," "at least one" and "one or more than one."

As described in more detail below, a method of increasing expression of an heterologous protein of interest in a plant or portion of the plant is provided. The method comprises:

i) treating the plant or portion of the plant with a jasmonate-pathway activator;

ii) introducing a nucleotide sequence comprising a nucleic acid encoding the heterologous protein of interest and operably linked to a regulatory region derived from a DNA plant virus; into the plant or portion of the plant; and iii) incubating the plant or the portion of the plant under conditions to permit expression of the nucleotide sequence encoding the heterologous protein of interest, the increase in expression observed when an amount of the heterologous protein of interest extracted from the plant or portion of the plant is compared to the heterologous protein of interest produced in a second plant or portion of the second plant that comprises the same nucleotide sequence, and has been treated in an analogous manner, but has been not been treated with the jasmonate-pathway activator.

The steps of treating (step i) and introducing (step ii) may be combined so that the jasmonic pathway activator is introduced into the plant or portion of the plant at the same time, along with the nucleotide sequence.

Furthermore, a method of decreasing total host soluble protein in a plant or portion of the plant, so as to reduce background host protein and simplify purification of a heterologous protein of interest is provided. The method comprising, i) treating the plant or portion of the plant with a jasmonate-pathway activator;

ii) introducing a nucleotide sequence comprising a nucleic acid encoding a heterologous protein of interest and operably linked to a regulatory region derived from a DNA plant virus into the plant or portion of the plant; and iii) incubating the plant or the portion of the plant under conditions to permit expression of the nucleotide sequence encoding the heterologous protein of interest, the decrease of total host protein observed when an amount of the total host protein extracted from the plant or portion of the plant is compared to the total host protein produced in a second plant or portion of the second plant that comprises the same nucleotide sequence, and has been treated in an analogous manner, but that has been not been treated with the jasmonate-pathway activator.

The steps of treating (step i) and introducing (step ii) may be combined so that the jasmonic pathway activator is introduced into the plant or portion of the plant at the same time, along with the nucleotide sequence.

Additional a method is provided to increasing expression of an heterologous protein of interest in a transgenic plant or portion of the transgenic plant. The method comprising:

i) treating the transgenic plant or portion of the transgenic plant with a jasmonate-pathway activator, the transgenic plant or portion of the transgenic plant comprising a nucleotide sequence encoding the heterologous protein of interest operably linked to a regulatory region derived from a DNA plant virus; and ii) incubating the transgenic plant or the portion of the transgenic plant under conditions to permit expression of the nucleotide sequence encoding the heterologous protein of interest, the increase in expression observed when an amount of the heterologous protein of interest extracted from the transgenic plant or portion of the transgenic plant is compared to the heterologous protein of interest produced in a second transgenic plant or portion of the second transgenic plant that comprises the same nucleotide sequence, and has been treated in an analogous manner, but has been not been treated with the jasmonate-pathway activator.

The steps of treating (step i) and introducing (step ii) may be combined so that the jasmonic pathway activator is introduced into the plant or portion of the plant at the same time, along with the nucleotide sequence.

By "operatively linked" it is meant that the particular sequences interact either directly or indirectly to carry out an intended function, such as mediation or modulation of expression of a nucleic acid sequence. The interaction of operatively linked sequences may, for example, be mediated by proteins that interact with the operatively linked sequences.

Jasmonate signaling molecules are known to regulate plant responses to a variety of environmental stress, for example, wounding, drought stress, pathogen attack, or pest attack. The jasmonate pathway involves several signal transduction events. Following a primary wound or stress stimulus, a local and systemic signal is produced that induces jasmonate biosynthesis. Jasmonate interacts with outputs from the salicylic acid (reducing the salicyclic pathway), ethylene, and other signaling pathways. Signaling in the jasmonate pathway involves protein interactions that form a $SCF^{(COI1)}$ complex (an E3-ubiquitin ligase) and a CSN (COP9 Signalosome) complex. $SCF^{(COI1)}$ interacts with CSN to control most well-characterized jasmonate responses. For example, the CSN/$SCF^{(COI1)}$ complex targets transcriptional repressors, including JAZ proteins, for polyubiquitination and their modification or degradation by the 26S proteasome.

For example, MeJA and associated jasmonic acid-inducing signals such as wounding, herbivory or insect oral secretions are known to downregulate transcription of photosynthesis-related genes (Hermsmeier et al., 2001; Jung et al., 2007; Bilgin et al., 2010; Zubo et al., 2011; Duceppe et al., 2012). These suppressing effects may be associated with an accumulation of stress-related proteins and carbon-metabolizing enzymes in leaves, and may lead to reduced levels of RuBisCO (Giri et al., 2006; Wei et al., 2009; Duceppe et al., 2012; Ullmann-Zeunert et al., 2013; Mahajan et al., 2014; Leuzinger et al., 2013).

By "jasmonate-pathway activator", it is meant any compound that may activate the jasmonate-pathway within a plant. Without wishing to be bound by theory, a jasmonate-pathway activator may result in the degradation of jasmonate ZIM-domain (JAZ) proteins that bind and repress the activity of the transcription factors that modulate transcription of jasmonate-responsive genes. The interaction between $SCF^{(COI1)}$ and JAZ repressors may result in the degradation of the JAZ proteins and subsequent derepression of transcription factors, such as MYC2.

The activator may be a liquid, or a gas. For example, which is not to be considered limiting, the jasmonate-pathway activator may be methyl jasmonate:

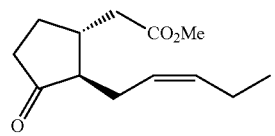

Methyl jasmonate (+)-6 jasmonic acid:

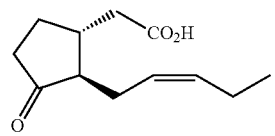

Jasmonic acid (-)-4 or, coronatine:

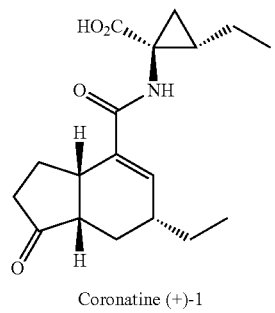 [SMILES: CC[C@H]1C=C(C(=O)N[C@@]2(C(=O)O)C[C@@H]2CC)[C@H]2CCC(=O)[C@H]2C1]

Coronatine (+)-1

Coronatine is a phytotoxin produced by the plant pathogen *Pseudomonas syringae* that is structurally related to methyl jasmonate (MeJA) and produces similar effects when applied to plants (Feys et al., 1994).

Other examples of jasmonate pathway activators include functional equivalents of MeJA, for example, but not limited to biologically active derivatives, analogues or precursors of jasmonic acid such as jasmonic acid (free), coronatin (microbial), polyunsaturated fatty acid (PUFA) precursors (e.g. alpha-linolenic acid) or their oxidation products, derivatives of jasmonic acid (excluding MeJA), for example, cis-jasmone, jasmonoyl isoleucine (JA-Ile), jasmonoyl ACC. Additionally, synthetic jasmonate analogues for example, BLUSh™ (prohydrojasmon (propyl-3-oxo-2-pentylcyclopentylacetate; available from Fine Agrochemicals Ltd.), and Compound I (5,7,9,10-tetrabromo derivative of methyl jasmonate, an active derivative) may be used.

The jasmonic pathway activator may be applied to the plant or portion of the plant by exposing (or pre-treating) the plant or plant portion to the activator for a period of time, for example from about 0 hours to 14 days, or any time therebetween, prior to introducing the nucleotide sequence encoding the protein of interest. For example, the plant or plant portion may be pre-treated with the activator compound from about 0, 0.5, 1.0, 1.5, 2.0, 2.5, 3.0, 3.5, 4.0, 4.5, 5.0, 5.0, 6.0, 7.0, 8.0, 9.0, 10.0, 12, 14, 16, 18, 20, 22, 24, 26, 28, 30, 32, 34, 36, 38, 40, 42, 44, 46, 48, 50, 552, 54, 56, 58, 60, 62, 64, 66, 68, 70, 72, 74, 76, 78, 80, 82, 84 hours, or any time therebetween, or the activator may be applied from about 0, 1, 2, 3, 4, 5, 6, 7, 8, 9, 10, 11, 12, 13, 14 days or any time therebetween, prior to introducing the nucleic acid encoding the protein of interest to the plant or plant portion.

The jasmonic pathway activator may also be applied to a transgenic plant or portion of the transgenic plant comprising a nucleotide sequence encoding a protein of interest by exposing the transgenic plant or transgenic plant portion to the activator for a period of time, for example from about 0 hours to 14 days, or any time therebetween, prior to extracting the protein of interest. For example, the transgenic plant or transgenic plant portion may be treated with the activator compound from about 0, 0.5, 1.0, 1.5, 2.0, 2.5, 3.0, 3.5, 4.0, 4.5, 5.0, 5.0, 6.0, 7.0, 8.0, 9.0, 10.0, 12, 14, 16, 18, 20, 22, 24, 26, 28, 30, 32, 34, 36, 38, 40, 42, 44, 46, 48, 50, 552, 54, 56, 58, 60, 62, 64, 66, 68, 70, 72, 74, 76, 78, 80, 82, 84 hours, or any time therebetween, or the activator may be applied from about 0, 1, 2, 3, 4, 5, 6, 7, 8, 9, 10, 11, 12, 13, 14 days or any time therebetween, prior to extracting the protein of interest from the transgenic plant or transgenic plant portion.

If the activator is in liquid form it may be sprayed onto the leaves and other organs of the plant as desired so that the activator may interact with the plant or plant part prior to the step of introducing the nucleotide sequence encoding the protein of interest into the plant or plant portion, or extracting the protein of interest from the transgenic plant or portion of the transgenic plant comprising a heterologous nucleotide sequence encoding the heterologous protein of interest. If the activator is a gas, then the plant or portion of the plant may be housed in a sealed environment so that the gas may interact with the plant or plant part prior to the step of introducing the nucleotide sequence encoding the protein of interest into the plant or plant portion, or prior to extracting the protein of interest from the transgenic plant or portion of the transgenic plant expressing the heterologous protein of interest.

Alternatively, if the nucleotide sequence is introduced into the plant or portion of the plant in a transient manner using a liquid medium within which the plant or portion of the plant is immersed for a period of time prior to introducing the nucleic acid encoding the protein of interest into the plant or plant portion, then the jasmonic-pathway activator may be introduced into the liquid medium. For example the plant or plant portion may be pretreated from about 0 hours to about 24 hours or any time therebetween, prior to introducing the nucleic acid encoding the protein of interest into the plant or plant portion. Alternatively, the step of exposing (treating) the plant or plant portion, and the step of introducing the nucleotide sequence encoding the protein of interest into the plant or plant portion, may be combined so that the jasmonic pathway activator is introduced into the liquid medium along with the nucleotide sequence, so that the jasmonic-pathway activator and nucleotide sequence are introduced into the plant or portion of the plant together.

As described herein, the jasmonic pathway activator may also be applied to a transgenic plant or portion of the transgenic plant comprising a heterologous nucleotide sequence operably linked to a regulatory region derived from a DNA plant virus, and that encodes a heterologous protein of interest, so as to increase expression of the heterologous protein of interest in the transgenic plant or portion of the transgenic plant. In this method, the transgenic plant or portion of the transgenic plant expressing the heterologous nucleotide sequence is treated with a jasmonate-pathway activator, and incubated for a period of time under conditions to permit expression of the heterologous nucleotide sequence encoding the heterologous protein of interest. The increase in expression of the heterologous protein of interest may be observed by comparing the yield of the heterologous protein of interest extracted from the transgenic plant or portion of the transgenic plant as compared to the heterologous protein of interest produced in a second transgenic plant or portion of the second transgenic plant that comprises the same nucleotide sequence, and has been treated in an analogous manner, but it has been not been treated with the jasmonate-pathway activator.

Without wishing to be bound by theory, by using a compound that is selective for inducing the jasmonate-pathway (i.e. a jasmonate-pathway activator), inhibitors of endogenous proteases may be activated, thereby reducing in vivo degradation of the heterologous protein of interest. For example, the transcription factor MYC2, that is involved in jasmonate signaling, positively regulates genes involved in wounding responses but negatively regulates genes involved in pathogen defense (Lorenzo et al., 2004). Furthermore, by activating the jasmonate pathway, the salicylic acid pathway may be down regulated. Activation of the salicylic acid pathway may result in an increase in activity of endogenous proteases. Therefore, by down-regulating the salicylic acid pathway, endogenous plant protease activity is reduced.

Using the methods described herein purification yield and contamination of the heterologous protein of interest with host proteins, their proteolytic fragments, or both the host proteins and their proteolytic fragments, and reducing protein degradation in crude extracts, may be improved by adjusting the ratio of heterologous protein of interest to host (native) proteins. Application of a jasmonic pathway activator was found to alter the proteome in leaves of plants and to elicited an enrichment of a recombinant, heterologous protein of interest. Without wishing to be bound by theory, this alteration may impact the specific and relative yields of the production of a heterologous protein of interest in plant tissue. Treatment of a plant or portion of a plant with a jasmonate-pathway activator induced a depletion of RuBisCO large and small subunit pools, and increased levels of jasmonate-inducible defense proteins (for example, thionins, Ser protease inhibitors and antimicrobial hydrolases). The increase in jasmonate-inducible defense proteins was reduced with agroinfiltration. However, a RuBisCO-depleted cellular environment was maintained in agroinfiltrated leaves, allowing for an effective enrichment of heterologous proteins of interest.

Compared to plants that were not treated with a jasmonic pathway activator (but that treated in an analogous manner), treatment using a jasmonic pathway activator resulted in an increased expression of a heterologous protein of interest. Additionally, treatment using a jasmonic pathway activator resulted in an approximately fivefold enrichment for a transiently expressed heterologous protein of interest relative to RuBisCO. The five fold enrichment of the heterologous protein of interest results from a greater than twofold depletion of RuBisCO and a twofold increase in the heterologous protein of interest mRNA transcripts, and a twofold increase in heterologous protein of interest levels on a fresh weight basis.

Therefore, treating a plant or portion of a plant with a jasmonic pathway activator results in an overall increase in yield of a heterologous protein of interest, and a relative increase in yield of a heterologous protein of interest compared to the levels of RuBisCO. By reducing RuBisCO levels, extraction and purification of the heterologous protein of interest may also be simplified due to reduced background protein contamination during the extraction process.

As described herein, increased expression of a heterologous nucleotide sequence encoding a protein of interest was observed when the nucleic acid encoding the protein of interest was operatively linked to a regulatory region comprising a promoter obtained from a plant DNA virus, for example the 35S promoter. No such increase in expression of the nucleotide sequence was observed when the regulatory region of a photosynthetic gene (for example the plastocyanin promoter) was used. Without wishing to be bound by theory, conditions that induce activation of the jasmonate pathway, the jasmonate-pathway activator, or both the conditions that induce activation of the jasmonate pathway and the jasmonate-pathway activator, may also be beneficial for the activity of a regulatory region comprising a promoter obtained from a plant DNA virus. Conditions that induce activation of the jasmonate pathway, the jasmonate-pathway activator, or both the conditions that induce activation of the jasmonate pathway and the jasmonate-pathway activator, may include stress conditions, or pathogen attack, including feeding on the plant by insects, and transmission of any associated plantDNA viruses from the insect to the plant.

The regulatory region comprising a promoter to be used in the methods described herein may be obtained from any DNA plant virus, including viruses of the Caulimoviridae, Geminiviridae and Nanoviridae families. Examples of promoters, which are not to be considered limiting, include promoters obtained from a gene of a virus of the Caulimoviridae family, including the 35S promoter of the cauliflower mosaic virus (Odell et al., 1985, Nature, 313: 810-812). Similarly, examples of promoters from a virus of the Geminiviridae and Nanoviridae families include those of the Rep and CP genes of the cotton leaf curl Burewala virus (Khan et al., 2015, PLoS ONE 10(3): e0121656) and those of the C1 to C11 of the Milk vetch dwarf virus (Shirasawa-Seo et al., 2005, J Gen Virol 86: 1851-1860), respectively.

As described herein there is provided an expression cassette comprising in series, a promoter or plant regulatory region obtained from a plant DNA virus, operatively linked to a nucleotide sequence of interest and a 3'UTR sequence and a terminator sequence. As one of skill in the art would appreciate, the termination (terminator) sequence may be any sequence that is active the plant host, for example the termination sequence may be a NOS terminator. "Expression cassette" refers to a nucleotide sequence comprising a nucleic acid of interest under the control of, and operably (or operatively) linked to, an appropriate promoter or other regulatory elements, for transcription of the nucleic acid of interest in a host cell.

The regulator region may also comprise additional regulatory elements, for example, but not limited to expression enhancers. Suitable expression enhancers include enhancers obtained from the CPMV 5'UTR as described in Sainsbury et. al. 2008 (Plant Physiol. 148:1212-1218); WO 2009/087391, PCT/CA2015/050009, PCT/CA2015/050240 (each of which is incorporated herein by reference). The expression enhancer may be operatively linked at the 5'end of the enhancer sequence with a regulatory region that is active in a plant, and operatively linked to a nucleotide sequence of interest at the 3'end of the expression enhancer, in order to drive expression of the nucleotide sequence of interest within a plant host.

By "nucleotide (or nucleic acid) sequence of interest", "coding region of interest", or protein of interest, it is meant any nucleotide sequence, or coding region (these terms may be used interchangeably) that is to be expressed within a host organism, for example a plant, to produce a protein of interest. Such a nucleotide sequence of interest may encode, but is not limited to, heterologous proteins, modified heterologous proteins, an industrial enzyme or a modified industrial enzyme, an agricultural protein or a modified agricultural protein, a helper protein, a protein supplement, a pharmaceutically active protein, a nutraceutical, a value-added product, or a fragment thereof for feed, food, or both feed and food use, an industrial enzyme for example, cellulase, xylanase, protease, peroxidase, subtilisin.

The nucleotide sequence of interest, or coding region of interest may also include a nucleotide sequence that encodes a pharmaceutically active protein, for example growth factors, growth regulators, antibodies, antigens, and fragments thereof, or their derivatives useful for immunization or vaccination and the like. Such proteins include, but are not limited to a protein that is a human pathogen, a viral protein, for example but not limited to one or more proteins from Respiratory syncytial virus (RSV), Rotavirus, influenza virus, human immunodeficiency virus (HIV), Rabies virus, human papiloma virus (HPV), Enterovirus 71 (EV71), or interleukins, for example one or more than one of IL-1 to IL-24, IL-26 and IL-27, cytokines, Erythropoietin (EPO), insulin, G-CSF, GM-CSF, hPG-CSF, M-CSF or combinations thereof, interferons, for example, interferon-alpha, interferon-beta, interferon-gama, blood clotting factors, for example, Factor VIII, Factor IX, or tPA hGH, receptors, receptor agonists, antibodies for example but not limited to Rituxan, neuropolypeptides, insulin, vaccines, growth factors for example but not limited to epidermal growth factor, keratinocyte growth factor, transformation growth factor, growth regulators, antigens, autoantigens, fragments thereof, or combinations thereof, a monoclonal antibody, a chimeric monoclonal antibody, a single chain monoclonal antibody, a virus like particle (VLP), or combinations thereof.

The protein of interest may also include an influenza hemagglutinin (HA; see WO 2009/009876, which is incorporated herein by reference). HA is a homotrimeric membrane type I glycoprotein, generally comprising a signal peptide, an HA1 domain, and an HA2 domain comprising a membrane-spanning anchor site at the C-terminus and a small cytoplasmic tail. Nucleotide sequences encoding HA are well known and are available (see, for example, the BioDefense and Public Health Database (Influenza Research Database; Squires et al., 2008 Nucleic Acids Research 36:D497-D503) at URL: biohealthbase.org/GSearch/home.do?decorator=Influenza; or the databases maintained by the National Center for Biotechnology Information (see URL: ncbi.nlm.nih.gov), both of which are incorporated herein by reference).

An HA protein may be of a type A influenza, a type B influenza, or is a subtype of type A influenza HA selected from the group of H1, H2, H3, H4, H5, H6, H7, H8, H9, H10, H11, H12, H13, H14, H15, and H16. In some aspects of the invention, the HA may be from a type A influenza, selected from the group H1, H2, H3, H5, H6, H7 and H9. Fragments of the HAs listed above may also be considered a protein of interest. Furthermore, domains from an HA type or subtype listed above may be combined to produce chimeric HA's (see for example WO2009/076778 which is incorporated herein by reference).

Examples of subtypes comprising HA proteins include A/New Caledonia/20/99 (H1N1), A/Indonesia/5/2006 (H5N1), A/chicken/New York/1995, A/herring gull/DE/677/88 (H2N8), A/Texas/32/2003, A/mallard/MN/33/00, A/duck/Shanghai/1/2000, A/northern pintail/TX/828189/02, A/Turkey/Ontario/6118/68 (H8N4), A/shoveler/Iran/G54/03, A/chicken/Germany/N/1949 (H10N7), A/duck/England/56 (H11N6), A/duck/Alberta/60/76 (H12N5), A/Gull/Maryland/704/77 (H13N6), A/Mallard/Gurjev/263/82, A/duck/Australia/341/83 (H15N8), A/black-headed gull/Sweden/5/99 (H16N3), B/Lee/40, C/Johannesburg/66, A/PuertoRico/8/34 (H1N1), A/Brisbane/59/2007 (H1N1), A/Solomon Islands 3/2006 (H1N1), A/Brisbane 10/2007 (H3N2), A/Wisconsin/67/2005 (H3N2), B/Malaysia/2506/2004, B/Florida/4/2006, A/Singapore/1/57 (H2N2), A/Anhui/1/2005 (H5N1), A/Vietnam/1194/2004 (H5N1), A/Teal/Hong-Kong/W312/97 (H6N1), A/Equine/Prague/56 (H7N7), A/HongKong/1073/99 (H9N2)).

The HA protein may be an H1, H2, H3, H5, H6, H7 or H9 subtype. For example, the H1 protein may be from the A/New Caledonia/20/99 (H1N1), A/PuertoRico/8/34 (H1N1), A/Brisbane/59/2007 (H1N1), A/Solomon Islands 3/2006 (H1N1), A/California/04/2009 (H1N1) or A/California/07/2009 (H1N1) strain. The H3 protein may also be from the A/Brisbane 10/2007 (H3N2), A/Wisconsin/67/2005 (H3N2), A/Victoria/361/2011 (H3N2), A/Texas/50/2012 (H3N2), A/Hawaii/22/2012 (H3N2), A/New York/39/2012 (H3N2), or A/Perth/16/2009 (H3N2) strain. In a further aspect of the invention, the H2 protein may be from the A/Singapore/1/57 (H2N2) strain. The H5 protein may be from the A/Anhui/1/2005 (H5N1), A/Vietnam/1194/2004 (H5N1), or A/Indonesia/5/2005 strain. In an aspect of the invention, the H6 protein may be from the A/Teal/Hong-Kong/W312/97 (H6N1) strain. The H7 protein may be from the A/Equine/Prague/56 (H7N7) strain, or H7 A/Hangzhou/1/2013, A/Anhui/1/2013 (H7N9), or A/Shanghai/2/2013 (H7N9) strain. In an aspect of the invention, the H9 protein is from the A/HongKong/1073/99 (H9N2) strain. In a further aspect of the invention, the HA protein may be from an influenza virus may be a type B virus, including B/Malaysia/2506/2004, B/Florida/4/2006, B/Brisbane/60/08, B/Massachusetts/2/2012-like virus (Yamagata lineage), or B/Wisconsin/1/2010 (Yamagata lineage). Non-limiting examples of amino acid sequences of the HA proteins from H1, H2, H3, H5, H6, H7, H9 or B subtypes include sequences as described in WO 2009/009876, WO 2009/076778, WO 2010/003225 (which are incorporated herein by reference). The influenza virus HA protein may be H5 Indonesia.

The HA may also be a chimeric HA, wherein a native transmembrane domain of the HA is replaced with a heterologous transmembrane domain. The transmembrane domain of HA proteins is highly conserved (see for example FIG. 1C of WO 2010/148511; which is incorporated herein by reference). The heterologous transmembrane domain may be obtained from any HA transmembrane domain, for example but not limited to the transmembrane domain from H1 California, B/Florida/4/2006 (GenBank Accession No. ACA33493.1), B/Malaysia/2506/2004 (GenBank Accession No. ABU99194.1), H1/Bri (GenBank Accession No. ADE28750.1), H1 A/Solomon Islands/3/2006 (GenBank Accession No. ABU99109.1), H1/NC (GenBank Accession No. AAP34324.1), H2 A/Singapore/1/1957 (GenBank Accession No. AAA64366.1), H3 A/Brisbane/10/2007 (GenBank Accession No. ACI26318.1), H3 A/Wisconsin/67/2005 (GenBank Accession No. AB037599.1), H5 A/Anhui/1/2005 (GenBank Accession No. ABD28180.1), H5 A/Vietnam/1194/2004 (GenBank Accession No. ACR48874.1), H5-Indo (GenBank Accession No. ABW06108.1). The transmembrane domain may also be defined by the following consensus amino acid sequence:

(SEQ ID NO: 1)
iLXiYystvAiSslXlXXmlagXsXwmcs

If the protein of interest is a VLP, then the VLP may comprise an HA0 precursor form, or the HA1 or HA2 domains retained together by disulphide bridges form. A VLP may have an average size of about 20 nm to 1 µm, or any amount therebetween, for example 60, 65, 70, 75, 80, 85, 90, 95, 100, 105, 110, 120, 130, 140, 150 160, 170, 180, 190, or 200 nm, or any amount therebetween, for example 100 nm, and may include a lipid membrane. The VLP may be enveloped, or non-enveloped, for example, a viral envelope protein, a viral structural protein, a viral capsid protein, or a viral coat protein. The VLP may further comprise one or more lipids, phospholipids, nucleic acids, membranes or the like.

The term "virus like particle" (VLP), or "virus-like particles" or "VLPs" refers to structures that self-assemble and comprise structural proteins such as influenza HA protein. VLPs are generally morphologically and antigenically similar to virions produced in an infection, but lack genetic information sufficient to replicate and thus are non-infectious. In some examples, VLPs may comprise a single protein species, or more than one protein species. For VLPs comprising more than one protein species, the protein species may be from the same species of virus, or may comprise a protein from a different species, genus, subfamily or family of virus (as designated by the ICTV nomenclature). In other examples, one or more of the protein species comprising a VLP may be modified from the naturally occurring sequence. VLPs may be produced in suitable host cells including plant and insect host cells. Following extraction from the host cell and upon isolation and further purification under suitable conditions, VLPs may be purified as intact structures.

The VLPs produced from influenza derived proteins, in accordance with the present invention do not comprise M1 protein. The M1 protein is known to bind RNA (Wakefield and Brownlee, 1989) which is a contaminant of the VLP preparation. The presence of RNA is undesired when obtaining regulatory approval for the VLP product, therefore a VLP preparation lacking RNA may be advantageous.

The HA may comprise a native, or a non-native signal peptide; the non-native signal peptide may be of plant origin. For example, the signal peptide may be a protein disulfide isomerase signal peptide (PDI). The native signal peptide may correspond to that of the hemagglutinin being expressed, or may correspond to a second hemagglutinin.

The present invention also provides nucleic acid molecules comprising sequences encoding an HA protein. The nucleic acid molecules may further comprise one or more regulatory regions operatively linked to the sequence encoding an HA protein. The nucleic acid molecules may comprise a sequence encoding an H1, H2, H3, H4, H5, H6, H7, H8, H9, H10, H11, H12, H13, H14, H15, H16 or HA from type B influenza. For example, the HA protein encoded by the nucleic acid molecule may be an H1, H2, H3, H5, H6, H7, H9 subtype an HA from type B. The H1 protein encoded by the nucleic acid may be from the A/New Caledonia/20/99 (H1N1), A/PuertoRico/8/34 (H1N1), A/Brisbane/59/2007 (H1N1), A/Solomon Islands 3/2006 (H1N1), A/California/04/2009 (H1N1) or A/California/07/2009 (H1N1) strain. The H3 protein encoded by the nucleic acid molecule may be from the A/Brisbane 10/2007 (H3N2), A/Wisconsin/67/2005 (H3N2), A/Victoria/361/2011 (H3N2), A/Texas/50/2012 (H3N2), A/Hawaii/22/2012 (H3N2), A/New York/39/2012 (H3N2), or A/Perth/16/2009 (H3N2) strain. The H2 protein encoded by the nucleic acid molecule may be from the A/Singapore/1/57 (H2N2) strain. The H5 protein encoded by the nucleic acid molecule A/Anhui/1/2005 (H5N1), A/Vietnam/1194/2004 (H5N1), or A/Indonesia/5/2005 strain. The H6 protein encoded by the nucleic acid molecule may be from the A/Teal/HongKong/W312/97 (H6N1) strain. The H7 protein encoded by the nucleic acid molecule may be from the A/Equine/Prague/56 (H7N7) strain, or H7 A/Hangzhou/1/2013, A/Anhui/1/2013 (H7N9), or A/Shanghai/2/2013 (H7N9) strain. Additional, the H9 protein encoded by the nucleic acid molecule may be from the A/HongKong/1073/99 (H9N2) strain. The HA protein encoded by the nucleic acid molecule may be from an influenza virus type B virus, including B/Malaysia/2506/2004, B/Florida/4/2006, B/Brisbane/60/08, B/Massachusetts/2/2012-like virus (Yamagata lineage), or B/Wisconsin/1/2010 (Yamagata lineage). Non-limiting examples of amino acid sequences of the HA proteins from H1, H2, H3, H5, H6, H7, H9 or B subtypes include sequences as described in WO 2009/009876, WO 2009/076778, WO 2010/003225 (which are incorporated herein by reference). The influenza virus HA protein may be H5 Indonesia.

The protein of interest (or coding region of interest) may comprise a native, or a non-native signal peptide; the non-native signal peptide may be of plant origin or obtained from an animal or bacterial polypeptide. The native signal peptide may correspond to that of the protein of interest being expressed, additionally, the signal peptide may be from a structural protein or hemagglutinin of a virus other than influenza. Non-limiting examples of a signal peptide that may be used is that of alfalfa protein disulfide isomerase (PDI SP; nucleotides 32-103 of Accession No. Z11499), or the patatin signal peptide (PatA SP; located nucleotides 1738-1806 of GenBank Accession number A08215). The nucleotide sequence of PatA SP for this accession number is:

(SEQ ID NO: 2)
ATGGCAACTACTAAAACTTTTTTAATTTTATTTTTTATGATATTAGCAAC
TACTAGTTCAACATGTGCT;

the amino acid sequence of patatin A signal peptide is:

(SEQ ID NO: 3)
MATTKTFLILFFMILATTSSTCA

The coding region of interest or the nucleotide sequence of interest may be expressed in any suitable plant host which is either transformed or comprises the nucleotide sequences, or nucleic acid molecules, or genetic constructs, or vectors of the present invention. Examples of suitable plant hosts include, but are not limited to, *Arabidopsis*, agricultural crops including for example canola, *Brassica* spp., maize, *Nicotiana* spp., (tobacco) for example, *Nicotiana benthamiana*, alfalfa, potato, sweet potato (*Ipomoea batatus*), ginseng, pea, oat, rice, soybean, wheat, barley, sunflower, cotton, corn, rye (*Secale cereale*), sorghum (*Sorghum bicolor, Sorghum vulgare*), safflower (*Carthamus tinctorius*).

The terms "biomass", "plant matter" or "portion of a plant" as used herein refer to any material derived from a plant. Biomass or plant matter may comprise an entire plant, or part of plant including the leaf, root, stem, flower, seed, it may also include any tissue of the plant, any cells of the plant, or any fraction of the plant, part or the plant, tissue or cell. Further, biomass or plant matter may comprise intracellular plant components, extracellular plant components, liquid or solid extracts of plants, or a combination thereof. Further, biomass or plant matter may comprise plants, plant cells, tissue, a liquid extract, or a combination thereof, from plant leaves, stems, fruit, roots or a combination thereof. A portion of a plant may comprise plant matter or biomass.

The protein of interest may be extracted and purified from the plant, or portion of the plant using known purification techniques including precipitation in the presence of a salt or PEG, chromatography, including size exclusion, ion-exchange, affinity or a combination thereof, filtration and the like (see Wilken, L. R. and Nikolov, Z. L. 2012, Biotechnol. Adv. 30, 419-433). The use of an extraction buffer at 4° C. and having a pH of 7.0 or above, may also reduce any endogenous proteolytic activity during extraction.

The terms "percent similarity", or "percent identity" when referring to a particular sequence are used for example as set forth in the University of Wisconsin GCG software program, or by manual alignment and visual inspection (see, e.g., Current Protocols in Molecular Biology, Ausubel et al., eds. 1995 supplement). Methods of alignment of sequences for comparison are well-known in the art. Optimal alignment of sequences for comparison can be conducted, using for example the algorithm of Smith & Waterman, (1981, Adv. Appl. Math. 2:482), by the alignment algorithm of Needleman & Wunsch, (1970, J. Mol. Biol. 48:443), by the search for similarity method of Pearson & Lipman, (1988, Proc. Nat'l. Acad. Sci. USA 85:2444), by computerized implementations of these algorithms (for example: GAP, BESTFIT, FASTA, and TFASTA in the Wisconsin Genetics Software Package, Genetics Computer Group (GCG), 575 Science Dr., Madison, Wis.).

An example of an algorithm suitable for determining percent sequence identity and sequence similarity are the BLAST and BLAST 2.0 algorithms, which are described in Altschul et al., (1977, Nuc. Acids Res. 25:3389-3402) and Altschul et al., (1990, J. Mol. Biol. 215:403-410), respectively. BLAST and BLAST 2.0 are used, with the parameters described herein, to determine percent sequence identity for the nucleic acids and proteins of the invention. For example the BLASTN program (for nucleotide sequences) may use as defaults a wordlength (W) of 11, an expectation (E) of 10, M=5, N=−4 and a comparison of both strands. For amino acid sequences, the BLASTP program may use as defaults a wordlength of 3, and expectation (E) of 10, and the BLOSUM62 scoring matrix (see Henikoff & Henikoff, 1989, Proc. Natl. Acad. Sci. USA 89:10915) alignments (B) of 50, expectation (E) of 10, M=5, N=−4, and a comparison of both strands. Software for performing BLAST analyses is publicly available through the National Center for Biotechnology Information (see URL: ncbi.nlm.nih.gov/).

By "regulatory region" "regulatory element" or "promoter" it is meant a portion of nucleic acid typically, but not always, upstream of the protein coding region of a gene, which may be comprised of either DNA or RNA, or both DNA and RNA. When a regulatory region is active, and in operative association, or operatively linked, with a gene of interest, this may result in expression of the gene of interest. A regulatory element may be capable of mediating organ specificity, or controlling developmental or temporal gene activation. A "regulatory region" includes promoter elements, core promoter elements exhibiting a basal promoter activity, elements that are inducible in response to an external stimulus, elements that mediate promoter activity such as negative regulatory elements or transcriptional enhancers. "Regulatory region", as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element may comprise a basal promoter element, responsible for the initiation of transcription, as well as other regulatory elements that modify gene expression.

There are several types of regulatory regions, including those that are developmentally regulated, inducible or constitutive. A regulatory region that is developmentally regulated, or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well. Examples of tissue-specific regulatory regions, for example see-specific a regulatory region, include the napin promoter, and the cruciferin promoter (Rask et al., 1998, J. Plant Physiol. 152: 595-599; Bilodeau et al., 1994, Plant Cell 14: 125-130). An example of a leaf-specific promoter includes the plastocyanin promoter (see U.S. Pat. No. 7,125,978, which is incorporated herein by reference).

If the nucleic acid sequence of interest encodes a product that is directly or indirectly toxic to the plant, then such toxicity may be reduced by selectively expressing the nucleotide sequence of interest within a desired tissue or at a desired stage of plant development. Alternatively, a promoter induced by the presence of methyl jasmonate, or other jasmonate-pathway activator, may also be used to drive the expression of a nucleotide sequence of interest as described herein.

An inducible regulatory region is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory region to activate transcription may be present in an inactive form, which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory region may be exposed to an inducer by externally applying the inducer to the cell or plant such as by spraying, watering, heating or similar methods. Inducible regulatory elements may be derived from either plant or non-plant genes (e.g. Gatz, C. and Lenk, I. R. P., 1998, Trends Plant Sci. 3, 352-358; which is incorporated by reference). Examples, of potential inducible promoters include, but not limited to, tetracycline-inducible promoter (Gatz, C., 1997, Ann. Rev. Plant Physiol. Plant Mol. Biol. 48, 89-108; which is incorporated by reference), steroid inducible promoter (Aoyama, T. and Chua, N. H., 1997, Plant J. 2, 397-404; which is incorporated by reference) and ethanol-inducible promoter (Salter, M. G., et al, 1998, Plant Journal 16, 127-132; Caddick, M. X., et al, 1998, Nature Biotech. 16, 177-180, which are incorporated by reference) cytokinin inducible IB6 and CKI1 genes (Brandstatter, I. and Kieber, J. J., 1998, Plant Cell 10, 1009-1019; Kakimoto, T., 1996, Science 274, 982-985; which are incorporated by reference) and the auxin inducible element, DRS (Ulmasov, T., et al., 1997, Plant Cell 9, 1963-1971; which is incorporated by reference).

A constitutive regulatory region directs the expression of a gene throughout the various parts of a plant and continuously throughout plant development. Examples of known constitutive regulatory elements include promoters associated with the CaMV 35S transcript. (p35S; Odell et al., 1985, Nature, 313: 810-812) or the Cassava Vein Mosaic Virus promoter, pCAS, (Verdaguer et al., 1996).

The term "constitutive" as used herein does not necessarily indicate that a nucleotide sequence under control of the constitutive regulatory region is expressed at the same level in all cell types, but that the sequence is expressed in a wide range of cell types even though variation in abundance is often observed.

The expression constructs as described herein may be present in a vector. The vector may comprise border sequences which permit the transfer and integration of the expression cassette into the genome of the organism or host. The construct may be a plant binary vector, for example a binary transformation vector based on pPZP (Hajdukiewicz, et al. 1994). Other example constructs include pBin19 (see Frisch, D. A., L. W. Harris-Haller, et al. 1995, *Plant Molecular Biology* 27: 405-409).

The constructs of the present invention can further comprise a 3' untranslated region (UTR). A 3' untranslated region contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' (SEQ ID NO: 4) although variations are not uncommon. Non-limiting examples of suitable 3' regions are the 3' transcribed non-translated regions containing a polyadenylation signal of *Agrobacterium* tumor inducing (Ti) plasmid genes, such as the nopaline synthase (Nos gene) and plant genes such as the soybean storage protein genes, the small subunit of the ribulose-1, 5-bisphosphate carboxylase gene (ssRUBISCO; U.S. Pat. No. 4,962,028; which is incorporated herein by reference), the promoter used in regulating plastocyanin expression (Pwee and Gray 1993; which is incorporated herein by reference). The termination (terminator) sequence may be obtained from the 3'UTR of the alfalfa plastocyanin gene.

If desired, the constructs of this invention may be further manipulated to include selectable markers. However, this may not be required. Useful selectable markers include enzymes that provide for resistance to chemicals such as an antibiotic for example, gentamycin, hygromycin, kanamycin, or herbicides such as phosphinothrycin, glyphosate, chlorosulfuron, and the like. Similarly, enzymes providing for production of a compound identifiable by colour change such as GUS (beta-glucuronidase), or luminescence, such as luciferase or GFP, may be used.

A vector may also include an expression enhancer as described herein. The expression enhancer may be positioned on a T-DNA which also contains a suppressor of gene silencing and NPTII. The polylinker may also encode one or two sets of 6× Histidine residues to allow the inclusion of N- or C-terminal His-tags to the protein of interest to facilitate protein purification.

Post-transcriptional gene silencing (PTGS) may be involved in limiting expression of transgenes in plants, and co-expression of a suppressor of silencing from the potato virus Y (HcPro) may be used to counteract the specific degradation of transgene mRNAs (Brigneti et al., 1998, *EMBO J.* 17, 6739-6746, which is incorporated herein by reference). Alternate suppressors of silencing are well known in the art and may be used as described herein (Chiba et al., 2006, Virology 346:7-14; which is incorporated herein by reference), for example but not limited to, TEV-p1/HC-Pro (Tobacco etch virus-p1/HC-Pro), BYV-p21, p19 of Tomato bushy stunt virus (TBSV p19; the construction of p19 is described in described in WO 2010/0003225, which is incorporated herein by reference), capsid protein of Tomato crinkle virus (TCV-CP), 2b of Cucumber mosaic virus; CMV-2b), p25 of Potato virus X (PVX-p25), p11 of Potato virus M (PVM-p11), p11 of Potato virus S (PVS-p11), p16 of Blueberry scorch virus, (BScV-p16), p23 of Citrus tristeza virus (CTV-p23), p24 of Grapevine leafroll-associated virus-2, (GLRaV-2 p24), p10 of Grapevine virus A, (GVA-p10), p14 of Grapevine virus B (GVB-p14), p10 of Heracleum latent virus (HLV-p10), or p16 of Garlic common latent virus (GCLV-p16).

Therefore, one or more suppressors of silencing, for example, but not limited to, HcPro, TEV-p1/HC-Pro, BYV-p21, TBSV p19, TCV-CP, CMV-2b, PVX-p25, rgscam, B2 protein from FHV, the small coat protein of CPMV, and coat protein from TCV, PVM-p11, PVS-p11, BScV-p16, CTV-p23, GLRaV-2 p24, GBV-p14, HLV-p10, GCLV-p16, or GVA-p10 may be co-expressed along with the comovirus-based expression cassette, geminivirus-derived amplification element, and the nucleic acid sequence encoding the protein of interest to further ensure high levels of protein production within a plant.

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421-463 (1988); Geierson and Corey, *Plant Molecular Biology*, 2d Ed. (1988); and Miki and Iyer, *Fundamentals of Gene Transfer in Plants*. In *Plant Metabolism,* 2d Ed. D T. Dennis, D H Turpin, D D Lefebrve, D B Layzell (eds), Addison Wesly, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example, Bilang, et al. (1991, *Gene* 100: 247-250), Scheid et al. (1991, *Mol. Gen. Genet.* 228: 104-112), Guerche et al. (1987, *Plant Science* 52: 111-116), Neuhause et al. (1987, *Theor. Appl Genet.* 75: 30-36), Klein et al., (2987, *Nature* 327: 70-73); Freeman et al. (1984, *Plant Cell Physiol*. 29: 1353), Howell et al. (1980, *Science* 208: 1265), Horsch et al. (1985, *Science* 227: 1229-1231), DeBlock et al., (1989, *Plant Physiology* 91: 694-701), Methods for Plant Molecular Biology (Weissbach and Weissbach, eds., Academic Press Inc., 1988), Methods in Plant Molecular Biology (Schuler and Zielinski, eds., Academic Press Inc., 1989), WO 92/09696, WO 94/00583, EP 331083, EP 175966, Liu and Lomonossoff (2002, *J Virol Meth,* 105:343-348), EP 290395; WO 8706614; U.S. Pat. Nos. 4,945,050; 5,036,006; and 5,100,792, U.S. patent application Ser. No. 08/438,666, filed May 10, 1995, and Ser. No. 07/951,715, filed Sep. 25, 1992, (all of which are hereby incorporated by reference).

Transient expression methods may be used to express the constructs of the present invention (see D'Aoust et al., 2009, *Methods in molecular biology*, Vol 483, pages41-50; Liu and Lomonossoff, 2002, *Journal of Virological Methods,* 105: 343-348; which is incorporated herein by reference). Alternatively, a vacuum-based transient expression method, as described by Kapila et al., (1997, *Plant Sci.* 122, 101-108; which is incorporated herein by reference), or WO 00/063400, WO 00/037663 (which are incorporated herein by reference) may be used. These methods may include, for example, but are not limited to, a method of Agro-inoculation or Agro-infiltration, syringe infiltration, however, other transient methods may also be used as noted above. With Agro-inoculation, Agro-infiltration, or syringe infiltration, a mixture of *Agrobacteria* comprising the desired nucleic acid enter the intercellular spaces of a tissue, for example the leaves, aerial portion of the plant (including stem, leaves and flower), other portion of the plant (stem, root, flower), or the whole plant. After crossing the epidermis the *Agrobacteria* infect and transfer t-DNA copies into the cells. The t-DNA is episomally transcribed and the mRNA translated, leading to the production of the protein of interest in infected cells, however, the passage of t-DNA inside the nucleus is transient.

Also considered part of this invention are transgenic plants, plant cells or seeds containing the gene construct of the present invention that may be used as a platform plant suitable for transient protein expression described herein. Methods of regenerating whole plants from plant cells are also known in the art (for example see Guerineau and Mullineaux (1993, Plant transformation and expression vectors. In: Plant Molecular Biology Labfax (Croy R R D ed) Oxford, BIOS Scientific Publishers, pp 121-148). In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Transgenic plants can also be generated without using tissue culture. Methods for stable transformation, and regeneration of these organisms are established in the art and known to one of skill in the art. Available techniques are reviewed in Vasil et al., (Cell Culture and Somatic Cell Genetics of Plants, Vol I, II and III, Laboratory Procedures and Their Applications, Academic Press, 1984), and Weissbach and Weissbach, (Methods for Plant Molecular Biology, Academic Press, 1989). The method of obtaining transformed and regenerated plants is not critical to the present invention.

If plants, plant portions or plant cells are to be transformed or co-transformed by two or more nucleic acid constructs, the nucleic acid construct may be introduced into the *Agrobacterium* in a single transfection event the nucleic acids are pooled, and the bacterial cells transfected as described. Alternately, the constructs may be introduced serially. In this case, a first construct is introduced to the *Agrobacterium* as described, the cells grown under selective conditions (e.g. in the presence of an antibiotic) where only the singly transformed bacteria can grow. Following this first selection step, a second nucleic acid construct is introduced to the *Agrobacterum* as described, and the cells grown under doubly-selective conditions, where only the doubly-transformed bacteria can grow. The doubly-transformed bacteria may then be used to transform a plant, plant portion or plant cell as described herein, or may be subjected to a further transformation step to accommodate a third nucleic acid construct.

Alternatively, if plants, plant portions, or plant cells are to be transformed or co-transformed by two or more nucleic acid constructs, the nucleic acid construct may be introduced into the plant by co-infiltrating a mixture of *Agrobacterium* cells with the plant, plant portion, or plant cell, each *Agrobacterium* cell may comprise one or more constructs to be introduced within the plant. In order to vary the relative expression levels within the plant, plant portion or plant cell, of a nucleotide sequence of interest within a construct, during the step of infiltration, the concentration of the various *Agrobacteria* populations comprising the desired constructs may be varied.

The present disclosure provides a method for generating a protein of interest, comprising the steps of providing a plant, or plant part, that expresses the expression system as described herein, harvesting a tissue, an organ, or the plant, in which the protein of interest has been expressed, and optionally, isolating the protein of interest from the tissue, organ or plant.

The present invention will be further illustrated in the following examples.

Materials and Methods

Plant Tissue Sampling and Elicitor Treatments

Forty-two day-old *N. benthamiana* plants grown in greenhouse were used for the experiments. Each plant was sprayed evenly with 50 ml of 0.5 mM, 1 mM or 2 mM MeJA in water containing 0.1% (v/v) Triton X-100 (Sigma-Aldrich, Mississauga ON, Canada), or with 50 ml of 1 mM arachidonic acid (Girard et al., 2007) in the same solvent, and transferred for seven days in a Conviron growth chamber (Conviron, Winnipeg MB, Canada). Plants sprayed with 50 ml of 0.1% (v/v) Triton X-100 in water were used in parallel as negative controls to avoid confounding effects due to experimental conditions. Two or three 1-cm² leaf discs were harvested from the third main stem leaf (see Robert et al., 2013) after seven days, as source material for protein and RNA extraction. The leaf samples were frozen immediately in liquid nitrogen and stored at −80° C. until protein or RNA extraction. Three to five biological (plant) replicates were used for each treatment, to allow for statistical treatment of the data.

Gene Constructs and Leaf Agroinfiltration

Two gene vectors were used for the agroinfiltration assays: an engineered pcambia2300 vector encoding the light and heavy chains of C5-1 fused to an N-terminal signal peptide sequence for cellular secretion (see Goulet et al., 2012 for details on gene construct); and the original ("empty") pcambia2300 binary vector (CAMBIA, Canberra, Australia) as a control for agroinfection. The two binary vectors were electroporated into *A. tumefaciens* strain LBA4404 and the cultures were maintained in Luria-Bertani (LB) medium supplemented with 50 µg/ml kanamycin and 50 µg/ml rifampicin. For infiltration, bacteria were grown to stable phase at 28° C. to an $OD_{600}$ of 1.0 and collected by centrifugation at 2,000 g. The bacterial pellets were resuspended in 10 mM 2-[N-morpholino] ethanesulfonic acid] (MES) buffer, pH 5.8, containing 100 µM acetosyringone and 10 mM $MgCl_2$. Leaf infiltration was performed using a needle-less syringe as described earlier (D'Aoust et al., 2009), after mixing the C5-1 antibody (or empty vector) agrobacterial suspension with an equal volume of bacterial suspension carrying a binary vector for the protein silencing suppressor p19 (Voinnet et al., 2003). Infiltrated tissue for molecular characterization was collected six days post-infection (i.e. seven days post-MeJA or arachidonate treatment), unless otherwise indicated. Three to five biological (plant) replicates were used for each treatment to allow for statistical analyses.

Protein Extraction, SDS-PAGE and Immunoblotting

Whole leaf proteins were extracted from three 1-cm² leaf discs in 400 µl of ice-cold 50 mM Tris-HCl, pH 7.5, containing 150 mM NaCl, by disrupting the leaf samples with tungsten carbide beads (Qiagen, Mississauga ON, Canada) in a Mini-Beadbeater apparatus (BioSpec, Bartlesville Okla., USA). The COMPLETE 'protease inhibitor cocktail' (Roche, Laval QC, Canada) was added in the extraction buffer before tissue disruption as specified by the supplier, except for those extracts dedicated to protease activity monitoring. Crude leaf extracts were clarified by centrifugation at 20,000 g for 30 min at 4° C., and total soluble proteins assayed according to Bradford (1976) with bovine serum albumin as a protein standard (Sigma-Aldrich). Electrophoretic separation of the proteins was performed by 10% (w/v) SDS-PAGE in reducing conditions (Laemmli, 1970), unless otherwise indicated. The resolved proteins were stained with Coomassie blue to visualize protein band patterns, or electrotransferred onto nitrocellulose membranes for immunodetection with appropriate primary and secondary antibodies. RuBisCO small subunit was detected using polyclonal IgG raised in rabbit against a synthetic small subunit peptide (Agrisera, Vännäs, Sweden) and alkaline phosphatase-conjugated goat anti-rabbit IgG as secondary antibodies (Sigma-Aldrich). RuBisCO large subunit was detected using polyclonal IgG raised in hen against a synthetic large subunit peptide (Agrisera) and alkaline phosphatase-conjugated goat anti-chicken IgG as secondary antibodies (Sigma-Aldrich). The 33-kDa pathogen-inducible PR-2 protein was detected using rabbit polyclonal IgY primary antibodies (Agrisera) and alkaline phosphatase-conjugated goat anti-rabbit IgG secondary antibodies (Sigma-Aldrich). C5-1 light and heavy chains were detected with alkaline phosphatase-conjugated goat anti-mouse IgG antibodies (Sigma-Aldrich).

Mass Spectrometry

Leaf proteins for MS identification (corresponding to protein gel areas in boxes A, B and C of FIG. 1b) were excised manually from the gels, put in 100 µl of Milli-Q water, and sent to the Eastern Québec Proteomics Center (Centre de Recherche du CHUL, Québec QC, Canada) for ion trap MS/MS analysis. In-gel protein digestion with sequencing grade trypsin (Promega, Madison Wis., U.S.A.) was performed in a MassPrep liquid handling robot (Waters, Milford Mass., U.S.A.) according to the provider's instructions. Peptide samples were resolved by online reversed-phase nanoscale capillary liquid chromatography and analyzed by electrospray mass spectrometry using a Thermo Surveyor MS pump connected to a LTQ linear ion trap mass spectrometer equipped with a nanoelectrospray ion source (ThermoFisher, San Jose Calif., U.S.A.). Peptide aliquots of 10 µl were loaded onto a 75-µm internal diameter BioBasic C18 picofrit column (New Objective, Woburn Mass., U.S.A.). The peptides were eluted along a water-acetonitrile/ 0.1 (v/v) formic acid gradient, at a flow rate of 200 nl/min obtained by flow splitting. Mass spectra were acquired under the data-dependent acquisition mode, using the Xcalibur software, v. 2.0. Each full MS scan (from 400 to 2000 m/z) was followed by MS/MS scans of the seven most intense precursor ions using collision-induced dissociation. The relative collisional fragmentation energy was set at 35%, and the dynamic exclusion function enabled with a 30-s exclusion duration.

Protein Identification

MS/MS spectral data were extracted using the ExtractMSn utility of Thermo's Bioworks application package, with no charge state deconvolution or deisotoping. Protein identities were assessed using the Mascot program, v. 2.3.02 (Matrix Science, London, U.K.) and the Open Source software X! Tandem (Craig et al., 2004). Both softwares were set up to search a custom database containing all known protein sequences of Solanaceae species (Taxonomy ID: 4070, for 39,896 proteins), *A. tumefaciens* protein sequences (12,554 proteins) and data sequences of protein contaminants commonly found in trypsin digests. The database was searched with a fragment ion mass tolerance of 0.50 Da and a parent ion tolerance of 2.0 Da. The iodoacetamide derivative of Cys residues was specified in both Mascot and X! Tandem as a fixed modification; citrullination of Arg residues and oxidation of Met residues were specified as variable modifications. MS/MS-based peptide and protein identifications were validated using Scaffold, v. 3.4.9 (Proteome Software, Portland OR, U.S.A.). Identifications were accepted if they included at least four peptides and could be established at greater than 95% probability as specified by the Peptide Prophet algorithm (Keller et al., 2002). Protein probabilities were assigned by the Protein Prophet algorithm as described by Nesvizhskii et al. (2003). Proteins that contained similar peptides and could not be differentiated based on MS/MS data were grouped to satisfy the principles of parsimony.

Real-Time RT PCR mRNA transcripts for C5-1 and *A. tumefaciens* virulence proteins VirB1 and VirE1 were assayed by real-time RT PCR using an ABI PRISM 7500 Fast real-time PCR apparatus, system version 2.0.1 (Applied Biosystems, Carlsbad Calif., U.S.A.). Total RNA was extracted from two 1-cm² leaf discs collected on the third main stem leaf (Robert et al., 2013) using the Qiagen RNeasy plant mini kit (Qiagen), following the supplier's instructions. RNA samples were treated with DNase I (Roche Diagnostics) to remove contaminant DNA and assessed for quality and quantity using a Nanodrop® ND-1000 spectrophotometer (NanoDrop Technologies, Wilmington Del., USA). First-strand cDNA was synthesized from 500 ng of total RNA using 4 units of Omniscript reverse transcriptase (Qiagen) and 1 µM of oligo-dT (15) nucleotides (Roche). PCR reactions contained 10 µl of Fast SYBR Green PCR Master Mix (Applied Biosystems), 2 µl of cDNA template, and 2.5 µl each of appropriate forward and reverse primers at 625 nM final concentration (Table 1). A no-template mixture control was included in each 96-well plate. Amplification rounds consisted of a 20-s denaturation step at 95° C., followed by 40 two-step cycles of 3 s at 95° C. and 30 s at 60° C. A dissociation curve analysis was performed after amplification with the SYBR Green Master Mix, and the cycle threshold of each sample was then compared to a DNA standard curve designed for each pair of primers. Standard curves were generated with 2 µl of cDNA template following the NEB Taq polymerase routine protocol (New England Biolabs, Pickering ON, Canada). Amplification products were purified using the Illustra GFX kit (GE Healthcare) and DNA standard curves were devised with serial dilutions of the purified PCR products in nuclease free-water (from $10^7$ to $10^2$ copies per µl). $C_t$ data were plotted against the corresponding number of transcript copies. All amplifications were carried out in duplicate.

Table 1: Forward and Reverse Oligonucleotide Primers Used for Real-Time RT PCR Assays

TABLE 1

Forward and reverse oligonucleotide primers used for real-time RT PCR assays

| Gene (protein | Forward | Reverse Annealing temperature(°C.) Amplicon (bp) |
|---|---|---|
| C5-1 antibody heavy chain | CCAAAACGACACCCCCA TCT (SEQ ID NO: 5) | AGGTCACTGTCACTGG CTCA 60.5 120 (SEQ ID NO: 6) |
| C5-1 antibody light chain | ATCCCCTCCAGGTTCAG TGG (SEQ ID NO: 7) | CGTGAGAGGCCAGCTG TTAC 60.8 120 (SEQ ID NO: 8) |
| A. tumefaciens VirB1 | ACGAGGCGCTAAAATCC GAA (SEQ ID NO: 9) | GATTTGCCGTTGTCCT GGTG 60.0 121 (SEQ ID NO: 10) |
| A. tumefaciens VirE1 | GCCGATAGAGAGACCGG AGT (SEQ ID NO: 11) | AGATTGTCTTCTGGGA GCGG 60.0 135 (SEQ ID NO: 12) |

Bacterial Counts

Bacterial loads in leaves were determined by the counting of CFU on LB agar plates coated with bacteria recovered at different moments from the third main stem leaf. Each replicate consisted of two 1-cm² leaf discs collected 0, 2, 4 or 6 days post-agroinfiltration. The leaf discs were homogenized in 10 mM MES buffer, pH 5.8, containing 10 mM MgCl$_2$ in the BioSpec Mini-Beadbeater (see Protein extraction, SDS-PAGE and immunoblotting, above). The resulting suspensions were dilution-plated on LB medium supplemented with kanamycin (50 mg/ml) and incubated at 28° C. until CFU counting after two days.

Protease Assays

Protease activities were assayed by the monitoring of substrate hydrolysis progress curves (Goulet et al., 2012) using the following synthetic fluorigenic substrates (Peptides International, Louisville Ky., USA): Z-Phe-Arg-methylcoumarin (MCA) for cathepsin L-like CIA Cys proteases, Z-Arg-MCA for trypsin-like S1 Ser proteases, and MOCAc-Gly-Lys-Pro-Ile-Leu-Phe-Phe-Arg-Leu-Lys(Dnp)-D-Arg-NH$_2$ for cathepsin D/E-like A1 Asp proteases. Substrate hydrolysis by the leaf extract proteases (36 ng leaf protein per µl of reaction mixture) were allowed to proceed at 25° C. in 50 mM MES, pH 5.8, containing 10 mM L-Cys for the cathepsin L substrate. Protease activity levels were monitored using a Fluostar Galaxy microplate fluorimeter (BMG, Offenburg, Germany) with excitation and emission filters of 360 and 450 nm, respectively, for the MCA substrates; or of 340 and 400 nm, respectively, for the MOCAc substrate. Three independent (biological) replicates were used for each assay.

C5-1 Quantification

ELISA plates for C5-1 antibody quantification (Becton Dickinson, Mississauga ON, Canada) were coated with 3.75 μg/ml goat anti-mouse heavy chain-specific IgG1 (Sigma-Aldrich) in 50 mM carbonate buffer (pH 9.0) at 4° C. for 16-18 h. The plates were washed three times in 10 mM phosphate-buffered saline containing 0.1% (v/v) Tween 20 (PBS-T), blocked through a 1-h incubation at 37° C. in 1% (w/v) casein in phosphate-buffered saline (PBS) (Pierce, Rockford Ill., USA), and washed three times in PBS-T. A standard curve was generated for each plate with 0, 4, 8, 16, 24, 32, 40 and 60 ng/ml of purified mouse IgG1 (Sigma-Aldrich). All dilutions (controls and samples) were performed in a control extract obtained from leaf tissue infiltrated with a mock inoculum so that any matrix effect was eliminated. The plates were incubated with protein samples for 1 h at 37° C., washed three times in PBS-T and then incubated with peroxidase-conjugated goat anti-mouse IgG (H+L) antibodies (0.02 μg/ml in blocking solution) (Jackson ImmunoResearch) for 1 h at 37° C. After additional washes with PBS-T, the plates were incubated with the 3,3',5,5'-tetramethylbenzidine Sure Blue peroxidase substrate (KPL, Gaithersburg Md., USA). The reaction was stopped by the addition of 1 N HCl and the absorbance was read at 450 nm. Three independent (biological) replicates were used for each assay.

Statistical Analyses

Statistical analyses were performed using the SAS program v. 9.1 (SAS Institute, Cary N.C., USA). ANOVA and PROC GLM procedures were used to compare C5-1 yields among treatments, densitometry data and protease activities. Contrast calculations were made when the ANOVA was significant using an α▫value threshold of 5%. Student t-tests were performed to compare mRNA transcript numbers for *A. tumefaciens* virulence proteins and C5-1 chains in control and MeJA-treated plants.

Example 1 i) MeJA Induces Leaf Proteome Rebalancing in *N. benthamiana*

Forty-two day-old *N. benthamiana* plants were treated with 0.5, 1 or 2 mM MeJA to determine the effects of jasmonic acid signaling on the overall protein profile in leaf tissue (FIG. 1). On a fresh weight basis, mature leaves of MeJA-treated plants had their TSP contents reduced by 20 to 30% after seven days compared to non-treated control leaves, depending on the elicitor dose (ANOVA; $P<0.001$) (FIG. 1a). As observed with other Solanaceae (Lawrence et al., 2008; Duceppe et al., 2012; Ullman-Zeunert et al., 2013), MeJA treatment caused a strong depletion of RuBisCO large and small subunit pools in leaf extracts (FIG. 1b), estimated at 40% less than in controls for the 0.5 mM MeJA dose to more than 90% less for the 2 mM dose (ANOVA; $P<0.05$ for RbcL; $P<0.001$ for RbcS) (FIG. 1c). RuBisCO depletion was counterbalanced by the up-regulation of several proteins, notably in the ~30-kDa, ~25-kDa and ~6-kDa molecular mass ranges as visualized on Coomassie blue-stained gels following SDS-PAGE (FIG. 1b, boxes A, B and C). A shotgun proteomic analysis was conducted to identify the most abundant proteins in these mass ranges, based on a spectral count analysis of tandem mass spectrometry (MS/MS) peptides obtained from trypsin digests of protein bands in boxes A, B and C of FIG. 1b (Table 2). Most of the identified proteins were MeJA-inducible stress-related (or defense) proteins, notably including thionins, chitinases, Ser protease inhibitors of the Kunitz and proteinase inhibitor II protein families, and stress-related enzymes such as superoxide dismutase, carbonic anhydrase and thioredoxin peroxidase (see Table 3 for details on MS/MS peptide sequences).

A number of plants were infiltrated 24 h post-MeJA treatment with *A. tumefaciens* cells harbouring an 'empty' pCAMBIA2300 vector (Goulet et al., 2012), to assess whether MeJA-mediated alterations of the leaf proteome could be maintained over the usual six to seven-day period left following bacterial infection for recombinant protein expression. Agroinfiltration is known to trigger active secretion of PR proteins, including PR-2 (B-glucanases) and PR-3 (chitinase) proteins, in the *N. benthamiana* leaf apoplast, presumably involving the pathogen-inducible salicylic acid signaling pathway (Goulet et al., 2010). Three protein bands in the mass range of 25 to 33-kDa (corresponding to the PR-2 and PR-3 proteins) were strongly up-regulated in agroinfiltrated leaves, regardless of the MeJA dose applied (FIG. 1b). As a result of the antagonistic interactions between the jasmonate and salicylate signaling pathways (Derksen et al., 2013), PR protein induction in infiltrated leaves was associated with a strong reversal of the MeJA-mediated stress protein inductions detected in uninfected plants, resulting in very faint protein signals in boxes A, B and C six days post-infection (FIG. 1b). Both the large and small subunits of RuBisCO were found at less than 50% of their original content, in leaves treated with 1 or 2 mM MeJA relative to untreated plants (FIGS. 1b,c).

These data demonstrate the effectiveness of MeJA as a potent, pre-infection trigger of RuBisCO depletion in *N. benthamiana* leaves, and its use in reducing RuBisCO load while increasing recombinant protein relative content in crude protein extracts prior to post-recovery enrichment and purification.

TABLE 2

Stress-related proteins up-regulated in *N. benthamiana* leaves seven days post-MeJA treatment[1,2]

| Protein | Accession No.[3] | Species | No. spectral counts |
|---|---|---|---|
| Box A | | | |
| Acidic endochitinase | P17514 | *Nicotiana tabacum* | 34 |
| Carbonic anhydrase | A4DOJ8 | *Nicotiana benthamiana* | 30 |
| Kunitz-type protease inhibitor | A9UF61 | *Nicotiana alata* | 22 |
| Proteasome subunit β type-6 | Q9XG77 | *Nicotiana tabacum* | 14 |
| Superoxide dismutase | P22302 | *Nicotiana plumbaginifolia* | 12 |
| Chaperonin 21 | Q9M5A8 | *Solanum lycopersicum* | 12 |
| Box B | | | |
| Kunitz-type protease inhibitor | A9UF61 | *N. alata* | 40 |
| Thioredoxin peroxidase | Q8RVF8 | *N. tabacum* | 18 |
| Pathogenesis-related protein R | P13046 | *N. tabacum* | 18 |
| Proteasome subunit β type-6 | P93395 | *N. tabacum* | 16 |
| Superoxide dismutase [Fe] | P22302 | *N. plumbaginifolia* | 14 |
| Box C | | | |
| Flower-specific thionin | B2BLV8 | *N. tabacum* | 39 |
| Trypsin proteinase inhibitor | Q1WL50 | *N. benthamiana* | 11 |

[1] These proteins correspond to the most abundant protein species identified by LC-MS/MS in boxes A, B and C of FIG. 1b. Proteins identifications based on a minimal spectral count of 10 spectra are included in the list.
[2] Additional information on MS/MS sequences is available in Table 3.
[3] Accession numbers from the National Center for Biotechnology Information/GenBank database (see URL: ncbi.nlm.nih.gov).

TABLE 3

Matched unique peptides for stress-regulated proteins up-regulated in *N. benthamiana* leaves seven days post-MeJA treatment[1,2]

| Protein | Access No. | Source organism | No. spectra | Matched unique peptides |
|---|---|---|---|---|
| Box A | | | | |
| Acidic endochitinase Q | P17514 | *N. tabacum* | 34 | GPIQLTNR (SEQ ID NO: 13)<br>GPIQLTNRNNYEK (SEQ ID NO: 14)<br>NDAVEDR (SEQ ID NO: 15)<br>NDAVEDRIGYYR (SEQ ID NO: 16)<br>QGIGSIVTSDLFNEMLK (SEQ ID NO: 17)<br>RYCGMLNVAPGENLDCYNQR (SEQ ID NO: 18)<br>YCGMLNVAPGENLDCYNQR (SEQ ID NO: 19)<br>YYGRGPIQLTNR (SEQ ID NO: 20)<br>YYGRGPIQLTNRNNYEK (SEQ ID NO: 21) |
| Carbonic anhydrase | A4D0J8 | *N. benthamiana* | 30 | ALMDLPENGSESTDFIENWVK (SEQ ID NO: 22)<br>EIYDKNPELIDELK (SEQ ID NO: 23)<br>EIYDKNPELIDELKK (SEQ ID NO: 24)<br>FLVFACSDSR (SEQ ID NO: 25)<br>IDEITAELQTSGFQSVHPVDR (SEQ ID NO: 26)<br>IDEITAELQTSGFQSVHPVDRIK (SEQ ID NO: 27)<br>IKTGFDYFKK (SEQ ID NO: 28)<br>NIANMVPPYDK (SEQ ID NO: 29)<br>NIANMVPPYDKTK (SEQ ID NO: 30)<br>TGFDYFK (SEQ ID NO: 31)<br>TGFDYFKK (SEQ ID NO: 32)<br>VENILVIGHSACGGIK (SEQ ID NO: 33)<br>VSPSHVLNFQLGEAFMVR (SEQ ID NO: 34) |
| Kunitz-type protease inhibitor | A9UF61 | *N. elate* | 22 | VGDPDLTAR (SEQ ID NO: 35)<br>FVTTHSR (SEQ ID NO: 36)<br>LCVNQTVWK (SEQ ID NO: 37)<br>VGDPDLTARGTR (SEQ ID NO: 38) |
| Proteasome subunit B type-6 | Q9XG77 | *N. tabacum* | 14 | AAGITSIGVR (SEQ ID NO: 39)<br>EQEAINFLEK (SEQ ID NO: 40)<br>GKDSVCVVTQK (SEQ ID NO: 41)<br>HITIFSPEGR (SEQ ID NO: 42)<br>LFQVEYAFK (SEQ ID NO: 43)<br>LLDQTSVSHLFPITK (SEQ ID NO: 44)<br>NEAAEFR (SEQ ID NO: 45)<br>TLVQQAR (SEQ ID NO: 46)<br>VLTTEEIDEHLTAISERD (SEQ ID NO: 47)<br>YLGLLATGMTADAR (SEQ ID NO: 48) |
| Superoxide dismutase | P22302 | *N. plumbaginifolia* | 12 | AAAATQFGSGWAWLAYKPEEK (SEQ ID NO: 49)<br>AAAATQFGSGWAWLAYKPEEKK (SEQ ID NO: 50)<br>AYVDNLNK (SEQ ID NO: 51)<br>AYVDNLNKQIDGTELDGK (SEQ ID NO: 52)<br>DFGSYDAFVK (SEQ ID NO: 53)<br>DFGSYDAFVKEFK (SEQ ID NO: 54)<br>KFELQPPPYPMDALEPHMSSR (SEQ ID NO: 55)<br>LVSWEAVSSR (SEQ ID NO: 56)<br>QIDGTELDGK (SEQ ID NO: 57)<br>QIDGTELDGKTLEDIILVTYNK (SEQ ID NO: 58)<br>RPDYISIFMEK (SEQ ID NO: 59)<br>TLEDIILVTYNK (SEQ ID NO: 60) |
| Chaperonin 21 | Q9M5A8 | *S. lycopersicum* | 12 | GADGSDYITLR (SEQ ID NO: 61)<br>KPLSVSPGNTVLYSK (SEQ ID NO: 62)<br>TAGGLLLTEAAK (SEQ ID NO: 63)<br>TGAQVIYSK (SEQ ID NO: 64) |

TABLE 3-continued

Matched unique peptides for stress-regulated proteins up-regulated in *N. benthamiana* leaves seven days post-MeJA treatment[1,2]

| Protein | Access No. | Source organism | No. spectra | Matched unique peptides |
|---|---|---|---|---|
| | | | | TKVDISVK (SEQ ID NO: 65)<br>VAEAEEKTAGGLLLTEAAK (SEQ ID NO: 66)<br>VLIKVAEAEEK (SEQ ID NO: 67)<br>YAGSEFKGADGSDYITLR (SEQ ID NO: 68)<br>YAGTEVEFDGSK (SEQ ID NO: 69)<br>YTTLKPLGDR (SEQ ID NO: 70) |
| Box B | | | | |
| Kunitz-type protease inhibitor | A9UF61 | *N. elate* | 40 | VGDPDLTAR (SEQ ID NO: 71)<br>FVTTHSR (SEQ ID NO: 72)<br>LCVNQTVWK (SEQ ID NO: 73)<br>VGDPDLTARGTR (SEQ ID NO: 74) |
| Thioredoxin peroxidise | Q8RVF8 | *N. tabacum* | 18 | GLFIIDKEGVIQHSTINNLGIGR (SEQ ID NO: 75)<br>GSKEYFASI (SEQ ID NO: 76)<br>KSGGLGDLNYPLISDVTK (SEQ ID NO. 77)<br>LSEYIGK (SEQ ID NO: 78)<br>SGGLGDLNYPLISDVTK (SEQ ID NO: 79)<br>SVDETLR (SEQ ID NO: 80)<br>SYNVLIPDQGIALR (SEQ ID NO: 81)<br>TLQALQYVQDNPDEVCPAGWKPGEK (SEQ ID NO: 82) |
| Pathogenesis-related protein R | P13046 | *N. tabacum* | 18 | CPDAYSYPQDDPTSLFTCPSGTNYR (SEQ ID NO: 83)<br>TNCNFDGSGR (SEQ ID NO: 84)<br>TNEYCCTNGPGSCGPTDLSR (SEQ ID NO: 85)<br>TQGGCNNPCIVIK (SEQ ID NO: 86) |
| Proteasome subunit B type-6 | P93395 | *N. tabacum* | 16 | DGASGGVVR (SEQ ID NO: 87)<br>SGSAADSQIVSDYVR (SEQ ID NO: 88)<br>TSTGMYVANR (SEQ ID NO: 89)<br>YFLHQHTIQLGQPATVK (SEQ ID NO: 90) |
| Superoxide dismutase [Fe] | P22302 | *N. plumbaginifolia* | 14 | AAAATQFGSGWAWLAYKPEEK (SEQ ID NO: 91)<br>AYVDNLNK (SEQ ID NO: 92)<br>AYVDNLNKQIDGTELDGK (SEQ ID NO: 93)<br>DFGSYDAFVK (SEQ ID NO: 94)<br>DFGSYDAFVKEFK (SEQ ID NO: 95)<br>KFELQPPPYPMDALEPHMSSR (SEQ ID NO:96)<br>LVSWEAVSSR (SEQ ID NO: 97)<br>QIDGTELDGK (SEQ ID NO: 98)<br>QIDGTELDGKTLEDIILVTYNK (SEQ ID NO: 99)<br>RPDYISIFMEK (SEQ ID NO: 100)<br>TLEDIILVTYNK (SEQ ID NO: 101) |
| Box C | | | | |
| Flower-specific thionin | B2BLV8 | *N. tabacum* | 39 | ACISEKFTDGHCSK (SEQ ID NO: 102)<br>FTDGHCSK (SEQ ID NO: 103)<br>KACISEK (SEQ ID NO: 104)<br>KACISEKFTDGHCSK (SEQ ID NO: 105)<br>ACISEKFTDGHCSK (SEQ ID NO: 106)<br>ACISEK (SEQ ID NO: 107) |
| Trypsin proteinase inhibitor | Q1WL50 | *N. benthamiana* | 11 | GCTFECDPR (SEQ ID NO: 108)<br>ICTNCCAGK (SEQ ID NO: 109)<br>LCTNCCAGTK (SEQ ID NO: 110)<br>NRLCTNCCAGTK (SEQ ID NO: 111) |

TABLE 3-continued

Matched unique peptides for stress-regulated proteins up-regulated in N. benthamiana leaves seven days post-MeJA treatment[1,2]

| Protein | Access No. | Source organism | No. spectra | Matched unique peptides |
|---------|------------|-----------------|-------------|-------------------------|
|         |            |                 |             | YFSDDGTFVCEGESDPR (SEQ ID NO: 112) YFSDDGTFVCEGESDPRNPK (SEQ ID NO: 113) YFSDDGTFVCEGESDPRNPKPCPR (SEQ ID NO: 114) IAYGICPLS (SEQ ID NO: 115) IAYGVCPR (SEQ ID NO: 116) |

[1]These proteins correspond to the most abundant protein species identified by LC-MS/MS in boxes A, B and C of FIG. 1b.
[2]Accession numbers from the National Center for Biotechnology Information/GenBank database (see: ncbi.nlm.nih.gov).

ii) MeJA has Little Effect on the *N. benthamiana-A. tumefaciens* Interaction

Following agroinfiltration, a near complete reversal of MeJA up-regulating effects on defense proteins was observed, indicating a limited influence of jasmonate treatment on both the plant's ability to mount a PR protein-based defense response to bacterial infection, and the ability of the bacterium to transfect plant cells and persist normally into leaf tissue. To further examine the plant-bacterium interaction immunoblots for PR-2 proteins as a reference for PR protein induction in leaves (Goulet et al., 2010) was used, and mRNA transcript numbers of two agrobacterial virulence genes regulated by salicylate as markers for the transfection process (Yuan et al., 2007) (FIG. 2). Several studies have reported strong antagonistic effects for salicylic acid or functional homologues on jasmonate signaling, and divergent regulatory patterns for salicylate-inducible PR proteins and jasmonate-inducible defense proteins upon salicylate or MeJA treatment (Thaler et al., 2012).

In line with the Coomassie blue-stained protein profiles (FIG. 1b), MeJA sprayed at 0.5 or 1 mM had no significant effect on the expression of a constitutively expressed 33-kDa pathogen-inducible PR-2 protein in non-infiltrated leaves (ANOVA; P>0.05; FIG. 2a).

Salicylic acid is known to attenuate agroinfection in leaves (Veena et al., 2003; Yuan et al., 2007; Anand et al., 2008) via a downregulation of the bacterium vir regulon affecting virulence gene expression and T-DNA integration into host cells (Yuan et al., 2007). Plants defective in salicylic acid have been shown to be more susceptible to the pathogen, while plants over-producing this metabolite showed increased recalcitrance to infection (Yuan et al., 2007). Bacterial counts and real-time RT PCR assays were here performed to compare *Agrobacterium* cell numbers and mRNA transcript pools of virulence proteins in infiltrated leaves, with or without MeJA treatment, to look for a possible salicylate-repressing effect of the jasmonate derivative facilitating *Agrobacterium* growth and virulence genes expression (FIGS. 2b,c).

Similar numbers of bacteria were retrieved from the apoplast of control and MeJA-treated leaves, as determined from bacterial counts of 10 to 100 million colony-forming units (CFU) per ml of apoplast extract up to two days post-infiltration, to less than a million CFU after four or six days (FIG. 2b). DNA coding sequences for VirB1 and VirE1, two virulence proteins involved in T-DNA translocation into recipient host cells and subsequent integration into the nucleus, respectively (Lacroix et al., 2006), were used as salicylate-responsive bacterial markers for RT PCR assays. VirB1 expression was negatively altered in MeJA-treated leaves and no positive effect on transcription was observed for either gene seven days post-MeJA treatment despite the natural antagonistic effect of jasmonates on salicylate signaling (FIG. 2c).

These data confirm overall the onset of a strong defense response to bacterial infection in MeJA-treated and control leaves upon agroinfiltration, and no positive impact of MeJA pre-treatment on both this response and the bacterium's potency for gene transfection.

iii) MeJA has Little Effect on Protease Activities in Transfected Leaves

Enzymatic assays were carried out with synthetic peptide substrates to investigate the effect of MeJA treatment on protease activity in leaf crude extracts (FIG. 3). Endogenous proteases have a strong impact on recombinant protein yield in plant systems given their direct role in protein turnover either in planta during expression or ex planta upon tissue disruption for protein recovery (Benchabane et al., 2008). Protease profiles are influenced by different developmental or environmental factors in *N. benthamiana*, including leaf age, agrobacterial infection and recombinant protein expression (Robert et al., 2013). Keeping in mind the complex cross-talks between defense-related signaling pathways (Robert-Seilaniantz et al., 2011), the importance of secreted proteases upon pathogenic infection (Hörger and van der Hoorn, 2013; Ramirez et al., 2013; Höwing et al., 2014; Figueiredo et al., 2014) and the MeJA-mediated over-expression of protease inhibitors that could influence the activity of endogenous proteases in crude extracts (see FIG. 1b and Table 2), the impact of MeJA treatment on major endoprotease activities in control and agroinfiltrated leaves was assessed.

Protease activities measured in crude extracts represent net values reflecting both the relative abundance of protease and protease inhibitor molecules in the extraction medium upon tissue disruption, and the inhibitory specificity of the released inhibitors towards endogenous proteases (Benchabane et al., 2009). Cathepsin L-like Cys protease, trypsin-like Ser protease and cathepsin D/E-like Asp protease activities were assayed in crude extracts of control and MeJA-treated leaves harvested seven days post-MeJA treatment to document the basic long-term effect of jasmonate signaling on leaf protease profiles. MeJA had no impact on cathepsin L-like activity for the three tested doses (ANOVA; P>0.05) (FIG. 3a). Trypsin-like enzymes showed a minimal or no increase in activity for the 0.5 and 1 mM doses (P<0.001) (FIG. 3b) despite a concomitant up-regulation of Ser protease inhibitors in leaves (see Table 2). Cathepsin D/E-like activity showed a dose-dependent decrease seven days post-MeJA treatment in uninfiltrated plants (P<0.001), which was also observed in agroinfiltrated leaves (FIG. 3c). Cathepsin L-like (P<0.05) and trypsin-like (P<0.001) activities were up-regulated in infiltrated leaves six days post-infection, independent of MeJA pre-treatment (FIG. 3Sa,b).

These data suggest a possible role for Cys and Ser proteases upon bacterial infection and the onset of specific expression patterns for these enzymes in agroinfiltrated leaves, independent of MeJA-mediated protease inhibitor inductions. The data also point to the establishment of a rebalanced proteome in MeJA-treated leaves six days post-infiltration presenting, with a significantly depleted pool of RuBisCO subunits; and a strongly increased amounts of pathogen-inducible PR proteins.

iv) MeJA Treatment Increases the Accumulation of a Transiently Expressed Recombinant Protein Agroinfiltration assays were conducted to determine the impact of MeJA treatment on the expression and steady-state levels of a clinically useful recombinant protein transiently expressed in leaf tissue (FIG. 4). The human blood-typing monoclonal antibody C5-1 (Khoudi et al., 1999) was selected as a model given the wealth of information available on the expression, maturation and proteolytic processing of this protein in plant systems (Khoudi et al., 1999; Bardor et al., 2003; Sainsbury et al., 2008; Vezina et al., 2009; D'Aoust et al., 2009; Goulet et al., 2012; Robert et al., 2013). The light and heavy chains of C5-1 co-expressed in N. benthamiana leaves are detected on immunoblots as a high molecular weight, multi-band protein pattern following SDS-PAGE in non-reducing conditions, including a ~150-kDa, fully assembled version of the antibody and a number of smaller, yet active, fragments (Goulet et al., 2012; Robert et al., 2013). A major protein band of about 150 kDa was immunodetected using anti-IgG primary antibodies (FIG. 4a). Visually similar protein band patterns, with increased intensity, were observed in leaf extracts of MeJA-treated plants compared to control plants.

A quantitative enzyme-linked immunosorbent assay (ELISA) was performed to confirm the apparent positive effect of MeJA on antibody accumulation, and to define a possible dose-curve relation for the jasmonate-mediated response (FIG. 4b). Significantly higher amounts of antibody were measured in MeJA-treated leaves, to reach steady-state levels about 1.5 to 2.5 times the levels measured in control plants (ANOVA; P<0.05). The up-regulating effect of MeJA followed a quadratic curve, with a maximum yield value of ~425 µg/g leaf tissue measured at 1 mM MeJA compared to ~325 µg/g leaf tissue at 2 mM MeJA or less than 200 µg/g in control leaves (FIG. 4b). The effect of MeJA was also confirmed on a protein-relative basis to give a net yield of 70 ng antibody/µg soluble proteins (or ~7% TSP) in leaves treated with 1 mM MeJA, about twice the yield obtained with control leaves (P<0.05) (FIG. 4b). As inferred from real-time RT PCR data for plants sprayed with 1 mM MeJA, higher C5-1 yields in MeJA-treated leaves were associated with higher numbers of mRNA transcripts for both the light and heavy chains, about twofold the numbers measured in control leaf extracts (FIG. 4c).

No yield increase was observed when spraying MeJA 24 h post-infiltration (FIG. 4d) or when treating leaves 24 h before infiltration with arachidonic acid, a functional analogue of salicylic acid (Girard et al., 2007) (FIG. 4d).

Furthermore, a more than twofold decrease of C5-1 yield in N. benthamiana leaves sprayed with 1 mM MeJA 24 h before infiltration when the recombinant antibody was expressed under the control of the alfalfa plastocyanin promoter (U.S. Pat. No. 7,125,978, which is incorporated herein by reference).

Induction of the 33-kDa PR-2 protein in leaves transfected with the empty pCAMBIA2300 vector (see FIG. 2a) was similar in leaves transfected with the antibody-encoding vector (FIG. 5), suggesting a limited, if not null, impact of C5-1 antibody expression on the host plant's response to agroinfiltration. Our observations suggest overall the practical usefulness of pre-infiltration MeJA treatment to boost recombinant protein expression in N. benthamiana leaves, via a yet to be understood transcription-promoting effect of the jasmonate pathway.

All citations are hereby incorporated by reference.

The present invention has been described with regard to one or more embodiments. However, it will be apparent to persons skilled in the art that a number of variations and modifications can be made without departing from the scope of the invention as defined in the claims. The scope of the claims should not be limited by the preferred embodiments set forth in the examples, but should be given the broadest interpretation consistent with the description as a whole

REFERENCES

Anand, A., Uppalapati, S. R., Ryu, C. M., Allen, S. N., Kang, L., Tang, Y. H. and Mysore, K. S. (2008) Salicylic acid and systemic acquired resistance play a role in attenuating crown gall disease caused by Agrobacterium tumefaciens. Plant Physiol. 146, 703-715.

Bilgin, D. D., Zavala, J. A., Zhu, J., Clough, S. J., Ort, D. R. and DeLucia, E. H. (2010) Biotic stress globally down-regulates photosynthesis genes. Plant Cell Environ. 33, 1597-1613.

Chen, Y., Pang, Q., Dai, S., Wang, Y., Chen, S. and Yan, X. (2011) Proteomic identification of differentially expressed proteins in Arabidopsis in response to methyl jasmonate. J. Plant Physiol. 168, 995-1008.

Craig, R., Cortens, J. P. and Beavis, R. C. (2004) Open source system for analyzing, validating, and storing protein identification data. J. Proteome Res. 3, 1234-1242.

D'Aoust, M.-A., Lavoie, P.-O., Belles-Isles, J., Bechtold, N., Martel, M. and Vezina, L.-P. (2009) Transient expression of antibodies in plants using syringe agroinfiltration. Meth. Mol. Biol. 483, 41-50.

Derksen, H., Rampitsch, C. and Daayf, F. (2013) Signaling cross-talk in plant disease resistance. Plant Sci. 207, 79-87.

Duceppe, M.-O., Cloutier, C. and Michaud, D. (2012) Wounding, insect chewing and phloem sap feeding differentially alter the leaf proteome of potato, Solanum tuberosum L. Proteome Sci. 10, 73.

Feys, B., Benedetti, C. E., Penfold, C. N., and Turner, J. G. (1994). Arabidopsis mutants selected for resistance to the phytotoxin coronatine are male sterile, insensitive to methyl jasmonate, and resistant to a bacterial pathogen. Plant Cell 6: 751-759.

Figueiredo, A., Monteiro, F. and Sabastiana, M. (2014) Subtilisin-like proteases in plant-pathogen recognition and immune priming: a perspective. Front. Plant Sci. 5, 739.

Gaeda, D., Valdes, R., Escobar, A., Ares, D. M., Tones, E., Blanco, R., Ferro, W., Dorta, D., Gonzalez, M., Aleman, M. R., Padilla, S., Gomez, L., del Castillo, N., Mendoza, O., Urquiza, D., Soria, Y., Brito, J., Leyva, A., Borroto, C. and Gavilondo, J. V. (2007) Detection of Rubisco and mycotoxins as potential contaminants of a plantibody against the hepatitis B surface antigen purified from tobacco. Biologicals 35, 309-315.

Giri, A. P., Wunsche, H., Mitra, S., Zavala, J. A., Muck, A., Svatos, A. and Baldwin, I. T. (2006) Molecular interactions between the specialist herbivore Manduca sexta (Lepidoptera, Sphingidae) and its natural host Nicotiana attenuata. VII. Changes in the plant's proteome. Plant Physiol. 142, 1621-1641.

Gomord, V. and Faye, L. (2004) Posttranslational modification of therapeutic proteins in plants. Curr. Opin. Plant Biol. 7, 171-181.

Goossens, A., Van Montagu, M. and Angenon, G. (1999) Co-introduction of an antisense gene for an endogenous seed storage protein can increase expression of a transgene in *Arabidopsis thaliana* seeds. FEBS Lett. 456, 160-164.

Goulet, C., Khalf, M., Sainsbury, F., D'Aoust, M.-A. and Michaud, D. (2012) A protease activity-depleted environment for heterologous proteins migrating towards the leaf cell apoplast. Plant Biotechnol. J. 10, 83-94.

Goulet, C., Goulet, C., Goulet, M.-C. and Michaud, D. (2010) 2-DE proteome maps for the leaf apoplast of *Nicotiana benthamiana*. Proteomics 10, 2536-2544.

Goulet, M.-C., Dallaire, C., Vaillancourt, L.-P., Khalf, M., Badri, A. M., Preradov, A., Duceppe, M.-O., Goulet, C., Cloutier, C. and Michaud, D. (2008) Tailoring the specificity of a plant cystatin toward herbivorous insect digestive cysteine proteases by single mutations at positively selected amino acid sites. Plant Physiol. 146, 1010-1019.

Hermsmeier, D., Schittko, U. and Baldwin, I. T. (2001) Molecular interactions between the specialist herbivore Manduca sexta (Lepidoptera, Sphingidae) and its natural host Nicotiana attenuata. I. Large-scale changes in the accumulation of growth- and defense-related plant mRNAs. Plant Physiol. 125, 683-700.

Hörger, A. C. and van der Hoorn, R. A. L. (2013) The structural basis of specific protease-inhibitor interactions at the plant-pathogen interface. Curr. Opin. Struct. Biol. 23, 842-850.

Höwing, T., Huesmann, C., Hoefle, C'', Nagel, M.-K., Isono, E., Hückelhoven, R. and Gietl, E. (2014) Endoplasmic reticulum KDEL-tailed cysteine endopeptidase 1 of *Arabidopsis* (AtCEP1) is involved in pathogen defense. Front. Plant Sci. 5, 58.

Jung, C., Lyou, S. H., Yeu, S., Kim, M. A., Rhee, S., Kim, M., Lee, J. S., Choi, Y. D. and Cheong, J. J. (2007) Microarray-based screening of jasmonate-responsive genes in *Arabidopsis thaliana*. Plant Cell Rep. 26, 1053-1063.

Jung, S.-K., Lindenmuth, B. E., McDonald, K. A., Hwang M. S., Nguyen Bui, M. Q., Falk, B. W., Uratsu, S. L., Phu, M. L. and Dandekar, A. M. (2014) *Agrobacterium tumefaciens* mediated transient expression of plant cell wall-degrading enzymes in detached sunflower leaves. Biotechnol. Progr. 30, 905-915.

Khoudi, H., Laberge, S., Ferullo, J. M., Bazin, R., Darveau, A., Castonguay, Y., Allard, G., Lemieux, R. and Vezina, L.-P. (1999) Production of a diagnostic monoclonal antibody in perennial alfalfa plants. Biotechnol. Bioeng. 64, 135-143.

Kim, Y.-M., Lee, J.-Y., Lee, T., Lee, Y.-H., Kim, S.-H., Kang, S.-H., Yoon, U.-H., Ha, S.-H. and Lim, S.-H. (2012) The suppression of the glutelin storage protein gene in transgenic rice seeds results in a higher yield of recombinant protein. Plant Biotechnol. Rep. 6, 347-353.

Lacroix, B., Li, J., Tzfira, T. and Citovsky, V. (2006) Will you let me use your nucleus? How *Agrobacterium* gets its T-DNA expressed in the host plant cell. Can. J. Physiol. Pharmacol. 84, 333-345.

Laemmli, U. K. (1970) Cleavage of structural proteins during the assembly of the head of bacteriophage T4. Nature 227, 680-685.

Leuzinger, K., Dent, M., Hurtado, J., Stahnke, J., Lai, H., Zhou, X. and Chen, Q. (2013) Efficient agroinfiltration of plants for high-level transient expression of recombinant proteins. J. Vis. Exp. 77, e50521.

Lorenzo, O., Chico, J. M., Sanchez-Serrano, J. J., and Solano, R. (2004). JASMONATE-INSENSITIVE1 encodes a MYC transcription factor essential to discriminate between different jasmonate-regulated defense responses in *Arabidopsis*. Plant Cell 16: 1938-1950.

Mahajan, N. S., Mishra, M., Tamhane, V. A., Gupta, V. S. and Gin, A. P. (2014) Stress inducible proteomic changes in Capsicum annuum leaves. Plant Physiol. Biochem. 74, 212-217.

Merlin, M., Gecchele, E., Capaldi, S., Pezzotti, M. and Avesani, L. (2014) Comparative evaluation of recombinant protein production in different biofactories: The green perspective. Biomed. Res. Int. 2014, ID 136419.

Noir, S., Börner, M., Takahashi, N., Ishida, T., Tsui, T.-L., Balbi, V., Shanahan, H., Sugimoto, K. and Devoto, A. (2013) Jasmonate controls leaf growth by repressing cell proliferation and the onset of endoreduplication while maintaining a potential stand-by mode. Plant Physiol. 161, 1930-1951.

Okada, K., Abe, H. and Arimura, G. (2015) Jasmonates induce both defense responses and communication in monocotyledonous and dicotyledonous plants. Plant Cell Physiol. 56, 16-27.

Peckham, G. D., Bugos, R. C. and Su, W. W. (2006) Purification of GFP fusion proteins from transgenic plant cell cultures. Prot. Expres. Purif. 49, 183-189.

Potenza, C., Aleman, L. and Sengupta-Gopalan, C. (2004) Targeting transgene expression in research, agricultural, and environmental applications: Promoters used in plant transformation. In Vitro Cell Dev. Plant 40, 1-22.

Ramirez, V., Lopez, A., Mauch-Mani, B., Gil, M. J. and Vera, P. (2013) An extracellular subtilase switch for immune priming in *Arabidopsis*. PLoS Pathog. 9, e1003445.

Robert-Seilaniantz, A., Grant, M. and Jones, J. D. (2011) Hormone crosstalk in plant disease and defence: more than just jasmonate-salicylate antagonism. Annu. Rev. Phytopathol. 49, 317-343.

Sack, M., Hofbauer, A., Fischer, R. and Stoger, E. (2015) The increasing value of plant-made proteins. Curr. Opin. Biotechnol. 32, 163-170.

Sainsbury, F., Lavoie, P. O., D'Aoust, M.-A., Vezina, L.-P. and Lomonossoff, G. P. (2008) Expression of multiple proteins using full-length and deleted versions of cowpea mosaic virus RNA-2. Plant Biotechnol. J. 6, 82-92.

Sainsbury, F., Varennes-Jutras, P., Goulet, M.-C., D'Aoust, M.-A. and Michaud, D. (2013) Tomato cystatin S1CYS8 as a stabilizing fusion partner for human serpin expression in plants. Plant Biotechnol. J. 11, 1058-1068.

Schmidt, M. A. and Herman, E. M. (2008) Proteome rebalancing in soybean seeds can be exploited to enhance foreign protein accumulation. Plant Biotechnol. J. 6, 832-842.

Shigemitsu, T., Ozaki, S., Saito, Y., Kuroda, M., Morita, S., Satoh, S. and Masumura, T. (2012) Production of human growth hormone in transgenic rice seeds: co-introduction of RNA interference cassette for suppressing the gene expression of endogenous storage proteins. Plant Cell Rep. 31, 539-549.

Stanton, M., Ull-ann-Zeunert, L., Wielsch, N., Bartram, S., Svatos, A., Baldwin, I. T. and Groten, K. (2013) Silencing ribulose-1,5-bisphosphate carboxylase/oxygenase expression does not disrupt nitrogen allocation to defense after simulated herbivory in Nicotiana attenuata. Plant Signal. Behay. 8, e27570.

Thaler, J. S., Humphrey, P. T. and Whiteman, N. K. (2012) Evolution of jasmonate and salicylate signal crosstalk. Trends Plant Sci. 17, 260-270.

Ullmann-Zeunert, L., Stanton, M. A., Wielsch, N., Bartram, S., Hummert, C., Svatos, A., Baldwin, I. T. and Groten, K. (2013) Quantification of growth-defense trade-offs in a common currency: nitrogen required for phenolamide biosynthesis is not derived from ribulose-1,5-bisphosphate carboxylase/oxygenase turnover. Plant J. 75, 417-429.

Vézina, L.-P., Faye, L., Lerouge, P., D'Aoust, M.-A., Marquet-Blouin, E., Burel, C., Lavoie, P.-O., Bardor, M. and Gomord, V. (2009) Transient co-expression for fast and high-yield production of antibodies with human-like N-glycans in plants. Plant Biotechnol. J. 7, 442-455.

Voinnet, O., Rivas, S., Mestre, P. and Baulcombe, D. (2003) An enhanced transient expression system in plants based on suppression of gene silencing by the p19 protein of tomato bushy stunt virus. Plant J. 33, 949-956.

Wei, Z., Hu, W., Lin, Q., Cheng, X., Tong, M., Zhu, L., Chen, R. and He, G. (2009) Understanding rice plant resistance to the Brown Planthopper (Nilaparvata lugens): a proteomic approach. Proteomics 9, 2798-2808.

Yuan, Z.-C., Edlind, M. P., Liu, P., Saenkham, P., Banta, L. M., Wise, A. A., Roznone, E., Binns, A. N., Kerr, K. and Nester, E. W. (2007) The plant signal salicylic acid shuts down expression of the vir regulon and activates quormone-quenching genes in Agrobacterium. Proc. Natl. Acad. Sci. 104, 11790-11795.

Zubo, Y. O., Yamburenko, M. V., Kusnetsov, V. V. and Börner, T. (2011) Methyl jasmonate, gibberellic acid, and auxin affect transcription and transcript accumulation of chloroplast genes in barley. J. Plant Physiol. 168, 1335-1344.

---

What is claimed is:

1. A method of increasing expression of a heterologous protein of interest in a plant or portion of the plant comprising:
   i) pretreating the plant or portion of the plant with a jasmonate-pathway activator for 1 to 14 days, prior to introducing a nucleotide sequence comprising a nucleic acid encoding the heterologous protein of interest into the plant or portion of the plant;
   ii) introducing the nucleotide sequence comprising the nucleic acid encoding the heterologous protein of interest into the plant or portion of the plant, the nucleic acid operably linked to a regulatory region derived from a DNA plant virus, wherein the regulatory region comprises a double 35S promoter of the cauliflower mosaic virus; and
   iii) incubating the plant or the portion of the plant under conditions to permit expression of the nucleotide sequence encoding the heterologous protein of interest, the increase in expression observed when an amount of the heterologous protein of interest extracted from the plant or portion of the plant is compared to the heterologous protein of interest produced in a second plant or portion of the second plant that comprises the same nucleotide sequence and has not been treated with the jasmonate-pathway activator.

2. The method of claim 1, wherein the jasmonate-pathway activator is methyl jasmonate, jasmonic acid, coronatine, or any biologically active derivative thereof.

3. The method of claim 1, wherein in the step of pretreating, the jasmonate-pathway activator is sprayed onto the plant or portion of the plant or added to growth media supporting the plant or portion of the plant.

4. The method of claim 3, wherein the jasmonate-pathway activator is a gas.

5. The method of claim 3, wherein the jasmonate-pathway activator is a liquid.

6. The method of claim 1, wherein in the step of pretreating (step i), the jasmonate-pathway activator is applied as a gas to the plant or portion of the plant, or the jasmonate-pathway activator is applied as a liquid and sprayed onto the plant or portion of the plant.

7. The method of claim 1, wherein the plant or portion of the plant is immersed in a liquid medium containing the nucleotide sequence and the jasmonate-pathway activator.

8. The method of claim 1 wherein the heterologous protein of interest is a human pathogen, a viral protein, an interleukin, a cytokine, erythropoietin, insulin, G-CSF, GM-CSF, hPG-CSF, M-CSF, an interferon, a blood clotting factor, a receptor, a receptor agonist, an antibody, a neuropolypeptide, a growth factor, a growth regulator, an antigen, an autoantigen, a monoclonal antibody, a chimeric monoclonal antibody, a single chain monoclonal antibody, a virus like particle (VLP), or combinations thereof.

9. A method of decreasing total host soluble protein in a plant or portion of the plant comprising,
   i) pretreating the plant or portion of the plant with a jasmonate-pathway activator for 1 to 14 days, prior to introducing a nucleotide sequence comprising a nucleic acid encoding a heterologous protein of interest into the plant or portion of the plant;
   ii) introducing the nucleotide sequence comprising the nucleic acid encoding the heterologous protein of interest into the plant or portion of the plant, the nucleic acid operably linked to a regulatory region derived from a DNA plant virus, wherein the regulatory region comprises a double 35S promoter of the cauliflower mosaic virus; and
   iii) incubating the plant or the portion of the plant under conditions to permit expression of the nucleotide sequence encoding the heterologous protein of interest, the increase in expression observed when an amount of the heterologous protein of interest extracted from the plant or portion of the plant is compared to the heterologous protein of interest produced in a second plant or portion of the second plant that comprises the same nucleotide sequence and has not been treated with the jasmonate-pathway activator.

10. The method of claim 9, wherein the jasmonate-pathway activator is methyl jasmonate, jasmonic acid, coronatine, or any biologically active derivative thereof.

11. The method of claim 9, wherein in the step of pretreating, the jasmonate-pathway activator is sprayed onto the plant or portion of the plant or added to growth media supporting the plant or portion of the plant.

12. The method of claim 9, wherein the jasmonate-pathway activator is a gas.

13. The method of claim 9, wherein the jasmonate-pathway activator is a liquid.

* * * * *